United States Patent
Logan et al.

(10) Patent No.: US 6,686,185 B1
(45) Date of Patent: Feb. 3, 2004

(54) 25934, A NOVEL FATTY ACID DESATURASE AND USES THEREFOR

(75) Inventors: Thomas Joseph Logan, Needham, MA (US); Maria Alexandra Glucksmann, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/723,806

(22) Filed: Nov. 28, 2000

Related U.S. Application Data

(60) Provisional application No. 60/187,455, filed on Mar. 7, 2000.

(51) Int. Cl.$^7$ ................................................ C12N 9/02
(52) U.S. Cl. ................ 435/189; 435/252.3; 435/320.1; 435/325; 536/23.2
(58) Field of Search ........................ 435/189, 6, 252.3, 435/320.1, 325; 536/23.2, 23.5

(56) References Cited

FOREIGN PATENT DOCUMENTS

| WO | WO 00/09754 | 2/2000 |
|---|---|---|
| WO | WO 01/53468 A2 | 7/2001 |

OTHER PUBLICATIONS

Ntambi et al. (1988) J. Biol. Chem., vol. 263, No. 33, pp. 17291–17300.*
Kaestner et al. (1989) J. Biol. Chem., vol. 264, No. 25, pp. 14755–14761.*
Strausberg et al. EST Database, Accession AI401562 (Feb. 8, 1999).*
Altschul et al., "Basic Local Alignment Search Tool," J. Mol. Biol. 215:403–410 (1990).
Altschul et al., "Gapped BLAST and PSI_BLAST: a new generation of protein database search programs," Nucleic Acids Research, 25(17):3389–3402 (1997).
Chanda (ed.), Current Protocols in Molecular Biology, 2000, vol. 4, John Wiley & Sons, Inc. (Table of Contents only).
Cho et al., "Cloning, Expression, and Fatty Acid Regulation of the Human Δ–5 Desaturase," Journal of Biological Chemistry, 274(52):37335–37339 (Dec. 24, 1999).
Goldberg et al., "Multiple–Dose Efficacy and Safety of an Extended–Release Form of *Niacin* in the Management of Hyperlipidemia," American Journal of Cardiology, 85:1100–1105 (2000).
Guyton, "Combination Drug Therapy for Combined Hyperlipidemia," Current Cardiology Reports, 1:244–250 (1999).
Guyton et al., "Treatment of Hyperlipidemia with Combined Niacin–Statin Regimens," American Journal of Cardiology, 82:82U–84U (1998).
International Human Genome Sequencing Consortium, "Initial sequencing and analysis of the human genome," NATURE 409:860–921 (Feb. 15, 2001).
Karlin et al., "Applications and statistics for multiple high–scoring segments in molecular sequences," Proc. Natl. Acad. Sci., 90:5873–5877 (Jun. 1993).

Karlin et al., "Methods for assessing the statistical significance of molecular sequence features by using general scoring schemes," Proc. Natl. Acad. Sci., 87:2264–2268 (Mar. 1990).
Myers et al., "Optimal alignments in linear space," CABIOS, 4(1):11–17(1998).
Mziaut et al., "The N terminus of microsomal Δ9 stearoyl–CoA desaturase contains the sequence determinant for its rapid degradation," Proc. Natl. Acad. Sci., 97(16):8883–8888 (Aug. 1, 2000).
Sambrook et al. (eds.), "Molecular Cloning—A Laboratory Manual," 1989, $2^{nd}$ Edition, Cold Spring Harbor Laboratory Press (Table of Contents only).
Shanklin et al., "Eight Histidine Residues Are Catalytically Essential in a Membrane–Associated Iron Enzyme, Stearoyl–CoA Desaturase, and Are Conserved in Alkane Hydroxylase and Xylene Monooxygenase," Biochemistry 33(43):12787–94 (1994).
Shanklin et al., "Mössbauer studies of alkane ω–hydroxylase: Evidence for a diiron cluster in an integral–membrane enzyme," Proc. Natl. Acad. Sci., 94:2981–2986 (Apr. 1997).
Sonnhammer et al., "Pfam: A Comprehensive Database of Protein Domain Families Based on Seed Alignments," PROTEINS 28:405–420 (1997).
Stukey et al., "The OLEI Gene of *Saccharomyces cerevisiae* Encodes the Δ9 Fatty Acid Desaturase and Can Be Functionally Replaced by the Rat Stearoyl–CoA Desaturase Gene," Journal of Biological Chemistry, 265(33):20144–20149 (Nov. 25, 1990).
Venter et al., "The Sequence of the Human Genome," SCIENCE 291:1304–1351 (Feb. 16, 2001).
Weintraub et al., "Anti–sense RNA as a molecular tool for genetic analysis," Trends In Genetics, (Jan. 1985).
GenBank Accession No. AI815730 (Jul. 9, 1999).
GenBank Accession No. AI816228 (Jul. 9, 1999).
GenBank Accession No. AI942480 (Mar. 14, 2000).
GenBank Accession No. AW131469 (Oct. 27, 1999).
Genbank Accession No. BE244746 (Oct. 3, 2001).
GenBank Accession No. BE515130 (Aug. 7, 2000).
GenBank Accession No. W28157 (May 8, 1996).

* cited by examiner

*Primary Examiner*—Elizabeth Slobodyansky
(74) *Attorney, Agent, or Firm*—Millennium Pharmaceuticals Inc.

(57) ABSTRACT

The invention provides isolated nucleic acids molecules, designated 25934 nucleic acid molecules, which encode a novel desaturase family member. The invention also provides antisense nucleic acid molecules, recombinant expression vectors containing 25934 nucleic acid molecules, host cells into which the expression vectors have been introduced, and nonhuman transgenic animals in which a 25934 gene has been introduced or disrupted. The invention still further provides isolated 25934 proteins, fusion proteins, antigenic peptides and anti-25934 antibodies. Diagnostic methods utilizing compositions of the invention are also provided. The invention also provides methods for modulating fatty acid metabolism utilizing the compositions of the invention. Accordingly, methods of treating, preventing and/or diagnosing cardiovascular disorders, such atherosclerosis, hypertriglyceridemia, hypercholesterolemia, and hyperlipidemia, are disclosed.

24 Claims, 9 Drawing Sheets

START SEQ ID NO:1

CCACGCGTCCGGACTAGTTCCATTTCCACAGCTCCTCCTCCCGGCCGCGCGCCCCTCCCGCCCCGCGCGCGCCTCCTC

TTTCTCGCGGCCGAGTTCAGCCCGGGCAGCCATATGGGGGATACGCCAGCAACAGACGCCGGCCGCCAAGATCTGCATC

CCTAGGCCACGCTAAGACCCTGGGGAAGAGCGCAGGAGCCCGGGAGAAGGGCTGGAAGGAGGGGACTGGACGTGCGGAG

AATTCCCCCCTAAAAGGCAGAAGCCCCCGCCCCCACCCTCGAGCTCCGCTCGGGCAGAGCGCCTGCCTGCCTGCCGCTG

START SEQ ID NO:2

| | | | | | | | M | P | G | P | A | T | D | A | G | K | I | P | F | 13 |
|---|---|---|---|---|---|---|---|---|---|---|---|---|---|---|---|---|---|---|---|---|
| CTGCGGGCGCCCACCTCGCCCAGCC | | | | | | | ATG | CCA | GGC | CCG | GCC | ACC | GAC | GCG | GGG | AAG | ATC | CCT | TTC | 39 |

SEQ ID NO:3

| C | D | A | K | E | E | I | R | A | G | L | E | S | S | E | G | G | G | G | P | 33 |
|---|---|---|---|---|---|---|---|---|---|---|---|---|---|---|---|---|---|---|---|---|
| TGC | GAC | GCC | AAG | GAA | GAA | ATC | CGT | GCC | GGG | CTC | GAA | AGC | TCT | GAG | GGC | GGC | GGC | GGC | CCG | 99 |

| E | R | P | G | A | R | G | Q | R | Q | N | I | V | W | R | N | V | V | L | M | 53 |
|---|---|---|---|---|---|---|---|---|---|---|---|---|---|---|---|---|---|---|---|---|
| GAG | AGG | CCA | GGC | GCG | CGC | GGG | CAG | CGG | CAG | AAC | ATC | GTC | TGG | AGG | AAT | GTC | GTC | CTG | ATG | 159 |

| S | L | L | H | L | G | A | V | Y | S | L | V | L | I | P | K | A | K | P | L | 73 |
|---|---|---|---|---|---|---|---|---|---|---|---|---|---|---|---|---|---|---|---|---|
| AGC | TTG | CTC | CAC | TTG | GGG | GCC | GTG | TAC | TCC | CTG | GTG | CTC | ATC | CCC | AAA | GCC | AAG | CCA | CTC | 219 |

| T | L | L | W | A | Y | F | C | F | L | L | A | A | L | G | V | T | A | G | A | 93 |
|---|---|---|---|---|---|---|---|---|---|---|---|---|---|---|---|---|---|---|---|---|
| ACT | CTG | CTC | TGG | GCC | TAC | TTC | TGC | TTC | CTC | CTG | GCC | GCT | CTG | GGT | GTG | ACA | GCT | GGT | GCC | 279 |

| H | R | L | W | S | H | R | S | Y | R | A | K | L | P | L | R | I | F | L | A | 113 |
|---|---|---|---|---|---|---|---|---|---|---|---|---|---|---|---|---|---|---|---|---|
| CAT | CGC | TTG | TGG | AGC | CAC | AGG | TCC | TAC | CGG | GCC | AAG | CTG | CCT | CTG | AGG | ATA | TTT | CTG | GCT | 339 |

| V | A | N | S | M | A | F | Q | N | D | I | F | E | W | S | R | D | H | R | A | 133 |
|---|---|---|---|---|---|---|---|---|---|---|---|---|---|---|---|---|---|---|---|---|
| GTC | GCC | AAC | TCC | ATG | GCT | TTC | CAG | AAT | GAC | ATC | TTC | GAG | TGG | TCC | AGG | GAC | CAC | CGA | GCC | 399 |

| H | H | K | Y | S | E | T | D | A | D | P | H | N | A | R | R | G | F | F | F | 153 |
|---|---|---|---|---|---|---|---|---|---|---|---|---|---|---|---|---|---|---|---|---|
| CAC | CAC | AAG | TAC | TCA | GAG | ACG | GAT | GCT | GAC | CCC | CAC | AAT | GCC | CGC | CGG | GGC | TTC | TTC | TTC | 459 |

| S | H | I | G | W | L | F | V | R | K | H | R | D | V | I | E | K | G | R | K | 173 |
|---|---|---|---|---|---|---|---|---|---|---|---|---|---|---|---|---|---|---|---|---|
| TCC | CAT | ATT | GGG | TGG | CTG | TTT | GTT | CGC | AAG | CAT | CGA | GAT | GTT | ATT | GAG | AAG | GGG | AGA | AAG | 519 |

Fig. 1A

```
L   D   V   T   D   L   L   A   D   P   V   V   R   I   Q   R   K   Y   Y   K   193
CTT GAC GTC ACT GAC CTG CTT GCT GAT CCT GTG GTC CGG ATC CAG AGA AAG TAC TAT AAG 579

I   S   V   V   L   M   C   F   V   V   P   T   L   V   P   W   Y   I   W   G   213
ATC TCC GTG GTG CTC ATG TGC TTT GTG GTC CCC ACG CTG GTG CCC TGG TAC ATC TGG GGA 639

E   S   L   W   N   S   Y   F   L   A   S   I   L   R   Y   T   I   S   L   N   233
GAG AGT CTG TGG AAT TCC TAC TTC TTG GCC TCT ATT CTC CGC TAT ACC ATC TCA CTC AAC 699

I   S   W   L   V   N   S   A   A   H   M   Y   G   N   R   P   Y   D   K   H   253
ATC AGC TGG CTG GTC AAC AGC GCC GCC CAC ATG TAT GGA AAC CGG CCC TAT GAC AAG CAC 759

I   S   P   R   Q   N   P   L   V   A   L   G   A   I   G   E   G   F   H   N   273
ATC AGC CCT CGG CAG AAC CCA CTC GTC GCT CTG GGT GCC ATT GGT GAA GGC TTC CAT AAT 819

Y   H   H   T   F   P   F   D   Y   S   A   S   E   F   G   L   N   F   N   P   293
TAC CAT CAC ACC TTT CCC TTT GAC TAC TCT GCG AGT GAA TTT GGC TTA AAT TTT AAC CCA 879

T   T   W   F   I   D   F   M   C   W   L   G   L   A   T   D   R   K   R   A   313
ACC ACC TGG TTC ATT GAT TTC ATG TGC TGG CTG GGG CTG GCC ACT GAC CGC AAA CGG GCA 939
                                                            END SEQ ID NO:2
T   K   P   M   I   E   A   R   K   A   R   T   G   D   S   S   A   *           331
ACC AAG CCG ATG ATC GAG GCC CGG AAG GCC AGG ACT GGA GAC AGC AGT GCT TGA         993
                                                            END SEQ ID NO:3
ACTTGGAACAGCCATCCCACATGTCTGCCGTTGCAACCTCGGTTCATGGCTTTGGTTACAATAGCTCTCTTGTACATTG

GATCGTGGGAGGGGGCAGAGGGTGGGGAAGGAACGAGTCAATGTGGTTTGGGAATGTTTTTGTTTATCTCAAAATAATG
    END SEQ ID NO:1
TTGAAATACAATTATCAATG
```

Fig. 1B

```
Desaturase: domain 1 of 1, from 51 to 295: score 505.3, E = 4.7e-148
                   *->illgalHlgAlyllallptelkwktvivalllYvitGGlGITaGyHR
                      +l+++lHlgA y  + l++ +k  t ++a+++  + + lG+TaG+HR
        25934   51    VLMSLLHLGAVYS-LVLIPKAKPLTLLWAYFCFLLAA-LGVTAGAHR   95

LwsHRSYkaklpLrifLaifgtlAvQgsiyeWardHRaHHkysDTdaDPH
                      LwsHRSY+aklpLrifLa ++++A+Q++i+eW+rdHRaHHkys+TdaDPH
        25934   96    LWSHRSYRAKLPLRIFLAVANSMAFQNDIFEWSRDHRAHHKYSETDADPH  145 danRGFffSHvGWlLvkkhPavkekgkkldlsDLkaDpVvrFqhryYipl
                      +a+RGFffSH+GWl  v+kh++v+ekg+kld++DL+aDpVvr q++yY++
        25934  146    NARRGFFFSHIGWLFVRKHRDVIEKGRKLDVTDLLADPVVRIQRKYYKIS  195 mvlmgfiLPtLvpgylwGetfwggfvwagflRlvfvlhaTWcVNSaAHkf
                      +vlm+f++PtLvp+y WGe++w++++ a++lR+++ l+   W+VNSaAH++
        25934  196    VVLMCFVVPTLVPWYIWGESLWNSYFLASILRYTISLNISWLVNSAAHMY  245

GyrPyDsritPrnnwlvAlvtfGEGwHNfHHtFPyDYRnaekwkweyDlT
                      G+rPyD++i+Pr+n lvAl+++GEG+HN+HHtFP+DY ++e++   +++T
        25934  246    GNRPYDKHISPRQNPLVALGAIGEGFHNYHHTFPFDYSASEFG-LNFNPT  294 k<-*
                      +
        25934  295    T                                                   295
```

Fig. 3

```
CLUSTAL W (1.74) multiple sequence alignment

Homo   (SEQ ID NO:7)  MPAHLLQDDISSSYTTTTTTTAPPSRVLQNGGDKLETMPLYLEDDIRPD--IKDDIYDPT
Rat    (SEQ ID NO:8)  MPAHMLQ-EISSSYTTTTTTITEPPSGNLQNGREKMKKVPLYLEEDIRPE--MREDIHDPS
Gallus (SEQ ID NO:9)  MPAHLLQEEEFSSASSTTTVT---SRVTKNGNVIMEKD-LLNHDDVAAERGMVDDLFDET
25934                 ---------------------MPGPATDAGKIPFCDA----KEEIRAG--L-ESSEGGG
                                                .  . *   :        .::: .   : :.   .

Homo    YKDKEGPS-PKVEYVWRNIILMSLLHLGALYGITLIPTCKFYTWLWGVFYYFVSALGITA
Rat     YQDEEGPP-PKLEYVWRNIILMALLHVGALYGITLIPSSKVYTLLWGIFYYLISALGITA
Gallus  YREKEGPK-PPLRYVWRNIILMSLLHLGAIIGLTLIPSAKIQTLAWAILCFVLSALGITA
25934   GPERPGARGQRQNIVWRNVVLMSLLHLGAVYSLVLIPKAKPLTLLWAYFCFLLAALGVTA
          :. *.     .  ****:;**:***:**:  .:.***..*   *   *.  :  :.::***:**

Homo    GAHRLWSHRSYKARLPLRLFLIIANTMAFQNDVYEWARDHRAHHKFSETHADPHNSRRGF
Rat     GAHRLWSHRTYKARLPLRIFLIIANTMAFQNDVYEWARDHRAHHKFSETHADPHNSRRGF
Gallus  GSHRLWSHRSYKATLPLRIFLTIANSMAFQNDIYEWARDHRVHHKFSETHADPHNAMRGY
25934   GAHRLWSHRSYRAKLPLRIFLAVANSMAFQNDIFEWSRDHRAHHKYSETDADPHNARRGF
        *:*******:*:* ****:** ;**:******:;**:****.***;***.*****:  **:

Homo    FFSHVGWLLVRKHPAVKEKGSTLDLSDLEAEKLVMFQRRYYKPGLLLMCFILPTLVPWYF
Rat     FFSHVGWLLVRKHPAVKEKGGKLDMSDLKAEKLVMFQRRYYKPGLLLMCFILPTLVPWYC
Gallus  FFSHMAWLLVRKHPDVIEKGQKLDLSDLKADKVVMFQRRYYKPSVVLLCFTLPTLVPWYF
25934   FFSHIGWLFVRKHRDVIEKGRKLDVTDLLADPVVRIQRKYYKISVVLMCFVVPTLVPWYI
        ****:..**:****   * *** .**:;**  *:  :*  :***   .;:*:**  :*******

Homo    WGETFQNSVFVATFLRYAVVLNATWLVNSAAHLFGYRPYDKNISPRENILVSLGAVGEGF
Rat     WGETFLHSLFVSTFLRYTLVLNATWLVNSAAHLYGYRPYDKNIQSRENILVSLGSVGEGF
Gallus  WDESIIISFFIPAILRYTLGLNATWLVNSAAHMFGNRPYDQNINPRENPLVSVGALGEGF
25934   WGESLWNSYFLASILRYTISLNISWLVNSAAHMYGNRPYDKHISPRQNPLVALGAIGEGF
        *.*::   *  *:;.;:***::    **   :********:;:*   ****;:*..*:* **;:*:;****

Homo    HNYHHSFPYDYSASEYRWHINFTTFFIDCMAALGLAYDRKKVSKAAILARIKRTGDGNYK
Rat     HNYHHAFPYDYSASEYRWHINFTTFFIDCMAALGLAYDRKKVSKAAVLARIKRTGDGSHK
Gallus  HNYHHTFPYDYSTSEFGWRFNLTTAFIDLMCLLGLASDRKKVSKEVILARKMRTGDSHK
25934   HNYHHTFPFDYSASEFGLNFNPTTWFIDFMCWLGLATDRKRATKPMIEARKARTGDSSA-
        *****:**:***:***;.:*  ** ***  *.  ****  ***:;:*   ;  **   ****..

Homo    SG
Rat     SG
Gallus  SG
25934   --
```

Fig. 8

SEQUENCE LISTING

<160> NUMBER OF SEQ ID NOS: 9

<210> SEQ ID NO 1
<211> LENGTH: 1512
<212> TYPE: DNA
<213> ORGANISM: Homo sapiens
<220> FEATURE:
<221> NAME/KEY: CDS
<222> LOCATION: (342)...(1331)

<400> SEQUENCE: 1

```
ccacgcgtcc ggactagttc catttccaca gctcctcctc cccggccgcg cgccctccc      60 gccccgcgcg cgcctcctct ttctcgcggc cgagttcagc ccgggcagcc atatggggga    120
tacgccagca acagacgccg gccgccaaga tctgcatccc taggccacgc taagaccctg    180
gggaagagcg caggagcccg ggagaagggc tggaaggagg ggactggacg tgcggagaat    240 tccccccctaa aaggcagaag ccccgcccc caccctcgag ctccgctcgg gcagagcgcc    300
tgcctgcctg ccgctgctgc gggcgccac ctcgcccagc c atg cca ggc ccg gcc     356
                                              Met Pro Gly Pro Ala
                                                1               5 acc gac gcg ggg aag atc cct ttc tgc gac gcc aag gaa gaa atc cgt      404
Thr Asp Ala Gly Lys Ile Pro Phe Cys Asp Ala Lys Glu Glu Ile Arg
              10                  15                  20 gcc ggg ctc gaa agc tct gag ggc ggc ggc ccg gag agg cca ggc          452
Ala Gly Leu Glu Ser Ser Glu Gly Gly Gly Pro Glu Arg Pro Gly
         25                  30                  35 gcg cgc ggg cag cgg cag aac atc gtc tgg agg aat gtc gtc ctg atg      500
Ala Arg Gly Gln Arg Gln Asn Ile Val Trp Arg Asn Val Val Leu Met
     40                  45                  50 agc ttg ctc cac ttg ggg gcc gtg tac tcc ctg gtg ctc atc ccc aaa      548
Ser Leu Leu His Leu Gly Ala Val Tyr Ser Leu Val Leu Ile Pro Lys
 55                  60                  65 gcc aag cca ctc act ctg ctc tgg gcc tac ttc tgc ttc ctc ctg gcc      596
Ala Lys Pro Leu Thr Leu Leu Trp Ala Tyr Phe Cys Phe Leu Leu Ala
 70                  75                  80                  85 gct ctg ggt gtg aca gct ggt gcc cat cgc ttg tgg agc cac agg tcc      644
Ala Leu Gly Val Thr Ala Gly Ala His Arg Leu Trp Ser His Arg Ser
                 90                  95                 100 tac cgg gcc aag ctg cct ctg agg ata ttt ctg gct gtc gcc aac tcc      692
Tyr Arg Ala Lys Leu Pro Leu Arg Ile Phe Leu Ala Val Ala Asn Ser
            105                 110                 115 atg gct ttc cag aat gac atc ttc gag tgg tcc agg gac cac cga gcc      740
Met Ala Phe Gln Asn Asp Ile Phe Glu Trp Ser Arg Asp His Arg Ala
        120                 125                 130 cac cac aag tac tca gag acg gat gct gac ccc cac aat gcc cgc cgg      788
His His Lys Tyr Ser Glu Thr Asp Ala Asp Pro His Asn Ala Arg Arg
    135                 140                 145 ggc ttc ttc ttc tcc cat att ggg tgg ctg ttt gtt cgc aag cat cga      836
Gly Phe Phe Phe Ser His Ile Gly Trp Leu Phe Val Arg Lys His Arg
150                 155                 160                 165 gat gtt att gag aag ggg aga aag ctt gac gtc act gac ctg ctt gct      884
Asp Val Ile Glu Lys Gly Arg Lys Leu Asp Val Thr Asp Leu Leu Ala
                170                 175                 180 gat cct gtg gtc cgg atc cag aga aag tac tat aag atc tcc gtg gtg      932
Asp Pro Val Val Arg Ile Gln Arg Lys Tyr Tyr Lys Ile Ser Val Val
            185                 190                 195
```

```
ctc atg tgc ttt gtg gtc ccc acg ctg gtg ccc tgg tac atc tgg gga    980
Leu Met Cys Phe Val Val Pro Thr Leu Val Pro Trp Tyr Ile Trp Gly
        200                 205                 210 gag agt ctg tgg aat tcc tac ttc ttg gcc tct att ctc cgc tat acc    1028
Glu Ser Leu Trp Asn Ser Tyr Phe Leu Ala Ser Ile Leu Arg Tyr Thr
    215                 220                 225 atc tca ctc aac atc agc tgg ctg gtc aac agc gcc gcc cac atg tat    1076
Ile Ser Leu Asn Ile Ser Trp Leu Val Asn Ser Ala Ala His Met Tyr
230                 235                 240                 245 gga aac cgg ccc tat gac aag cac atc agc cct cgg cag aac cca ctc    1124
Gly Asn Arg Pro Tyr Asp Lys His Ile Ser Pro Arg Gln Asn Pro Leu
                250                 255                 260 gtc gct ctg ggt gcc att ggt gaa ggc ttc cat aat tac cat cac acc    1172
Val Ala Leu Gly Ala Ile Gly Glu Gly Phe His Asn Tyr His His Thr
            265                 270                 275 ttt ccc ttt gac tac tct gcg agt gaa ttt ggc tta aat ttt aac cca    1220
Phe Pro Phe Asp Tyr Ser Ala Ser Glu Phe Gly Leu Asn Phe Asn Pro
        280                 285                 290 acc acc tgg ttc att gat ttc atg tgc tgg ctg ggg ctg gcc act gac    1268
Thr Thr Trp Phe Ile Asp Phe Met Cys Trp Leu Gly Leu Ala Thr Asp
    295                 300                 305 cgc aaa cgg gca acc aag ccg atg atc gag gcc cgg aag gcc agg act    1316
Arg Lys Arg Ala Thr Lys Pro Met Ile Glu Ala Arg Lys Ala Arg Thr
310                 315                 320                 325 gga gac agc agt gct tgaacttgga acagccatcc cacatgtctg ccgttgcaac    1371
Gly Asp Ser Ser Ala
                330 ctcggttcat ggctttggtt acaatagctc tcttgtacat tggatcgtgg gagggggcag    1431 agggtgggga aggaacgagt caatgtggtt tgggaatgtt tttgtttatc tcaaaataat    1491 gttgaaatac aattatcaat g                                               1512

<210> SEQ ID NO 2
<211> LENGTH: 330
<212> TYPE: PRT
<213> ORGANISM: Homo sapiens

<400> SEQUENCE: 2

Met Pro Gly Pro Ala Thr Asp Ala Gly Lys Ile Pro Phe Cys Asp Ala
1               5                   10                  15

Lys Glu Glu Ile Arg Ala Gly Leu Glu Ser Ser Glu Gly Gly Gly
            20                  25                  30

Pro Glu Arg Pro Gly Ala Arg Gly Gln Arg Gln Asn Ile Val Trp Arg
        35                  40                  45

Asn Val Val Leu Met Ser Leu Leu His Leu Gly Ala Val Tyr Ser Leu
    50                  55                  60

Val Leu Ile Pro Lys Ala Lys Pro Leu Thr Leu Leu Trp Ala Tyr Phe
65                  70                  75                  80

Cys Phe Leu Leu Ala Ala Leu Gly Val Thr Ala Gly Ala His Arg Leu
                85                  90                  95

Trp Ser His Arg Ser Tyr Arg Ala Lys Leu Pro Leu Arg Ile Phe Leu
            100                 105                 110

Ala Val Ala Asn Ser Met Ala Phe Gln Asn Asp Ile Phe Glu Trp Ser
        115                 120                 125

Arg Asp His Arg Ala His His Lys Tyr Ser Glu Thr Asp Ala Asp Pro
    130                 135                 140

His Asn Ala Arg Arg Gly Phe Phe Ser His Ile Gly Trp Leu Phe
145                 150                 155                 160
```

```
Val Arg Lys His Arg Asp Val Ile Glu Lys Gly Arg Lys Leu Asp Val
            165                 170                 175

Thr Asp Leu Leu Ala Asp Pro Val Val Arg Ile Gln Arg Lys Tyr Tyr
        180                 185                 190

Lys Ile Ser Val Val Leu Met Cys Phe Val Pro Thr Leu Val Pro
    195                 200                 205

Trp Tyr Ile Trp Gly Glu Ser Leu Trp Asn Ser Tyr Phe Leu Ala Ser
        210                 215                 220

Ile Leu Arg Tyr Thr Ile Ser Leu Asn Ile Ser Trp Leu Val Asn Ser
225                 230                 235                 240

Ala Ala His Met Tyr Gly Asn Arg Pro Tyr Asp Lys His Ile Ser Pro
                245                 250                 255

Arg Gln Asn Pro Leu Val Ala Leu Gly Ala Ile Gly Glu Gly Phe His
                260                 265                 270

Asn Tyr His His Thr Phe Pro Phe Asp Tyr Ser Ala Ser Glu Phe Gly
                275                 280                 285

Leu Asn Phe Asn Pro Thr Thr Trp Phe Ile Asp Phe Met Cys Trp Leu
        290                 295                 300

Gly Leu Ala Thr Asp Arg Lys Arg Ala Thr Lys Pro Met Ile Glu Ala
305                 310                 315                 320

Arg Lys Ala Arg Thr Gly Asp Ser Ser Ala
                325                 330

<210> SEQ ID NO 3
<211> LENGTH: 990
<212> TYPE: DNA
<213> ORGANISM: Homo sapiens

<400> SEQUENCE: 3
atgccaggcc cggccaccga cgcggggaag atccctttct gcgacgccaa ggaagaaatc      60
cgtgccgggc tcgaaagctc tgagggcggc ggcggcccgg agaggccagg cgcgcgcggg    120
cagcggcaga acatcgtctg gaggaatgtc gtcctgatga gcttgctcca cttgggggcc    180
gtgtactccc tggtgctcat ccccaaagcc aagccactca ctctgctctg gcctacttc     240 tgcttcctcc tggccgctct gggtgtgaca gctggtgccc atcgcttgtg gagccacagg    300
tcctaccggg ccaagctgcc tctgaggata tttctggctg tcgccaactc catggctttc    360
cagaatgaca tcttcgagtg gtccagggac accgagccc accaagta ctcagagacg      420 gatgctgacc ccacaatgc ccgccgggc ttcttcttct cccatattgg gtggctgttt    480
gttcgcaagc atcgagatgt tattgagaag gggagaaagc ttgacgtcac tgacctgctt    540
gctgatcctg tggtccggat ccagagaaag tactataaga tctccgtggt gctcatgtgc    600
tttgtggtcc ccacgctggt gccctggtac atctggggag agagtctgtg gaattcctac    660
ttcttggcct ctattctccg ctataccatc tcactcaaca tcagctggct ggtcaacagc    720
gccgcccaca tgtatggaaa ccggccctat gacaagcaca tcagccctcg cagaacccca    780
ctcgtcgctc tgggtgccat tggtgaaggc ttccataatt accatcacac ctttcccttt    840
gactactctg cgagtgaatt tggcttaaat tttaacccaa ccacctggtt cattgatttc    900
atgtgctggc tggggctggc cactgaccgc aaacgggcaa ccaagccgat gatcgaggcc    960
cggaaggcca ggactggaga cagcagtgct                                     990

<210> SEQ ID NO 4
<211> LENGTH: 248
<212> TYPE: PRT
```

```
<213> ORGANISM: Artificial Sequence
<220> FEATURE:
<223> OTHER INFORMATION: consensus sequence

<400> SEQUENCE: 4

Ile Leu Leu Gly Ala Leu His Leu Gly Ala Leu Tyr Leu Leu Ala Leu
 1               5                  10                  15

Leu Pro Thr Glu Leu Lys Trp Lys Thr Val Ile Val Ala Leu Leu Leu
                20                  25                  30

Tyr Val Ile Thr Gly Gly Leu Gly Ile Thr Ala Gly Tyr His Arg Leu
            35                  40                  45

Trp Ser His Arg Ser Tyr Lys Ala Lys Leu Pro Leu Arg Ile Phe Leu
        50                  55                  60

Ala Ile Phe Gly Thr Leu Ala Val Gln Gly Ser Ile Tyr Glu Trp Ala
65                  70                  75                  80

Arg Asp His Arg Ala His His Lys Tyr Ser Asp Thr Asp Ala Asp Pro
                85                  90                  95

His Asp Ala Asn Arg Gly Phe Phe Ser His Val Gly Trp Leu Leu
                100                 105                 110

Val Lys Lys His Pro Ala Val Lys Glu Lys Gly Lys Lys Leu Asp Leu
            115                 120                 125

Ser Asp Leu Lys Ala Asp Pro Val Val Arg Phe Gln His Arg Tyr Tyr
        130                 135                 140

Ile Pro Leu Met Val Leu Met Gly Phe Ile Leu Pro Thr Leu Val Pro
145                 150                 155                 160

Gly Tyr Leu Trp Gly Glu Thr Phe Trp Gly Phe Val Trp Ala Gly
                165                 170                 175

Phe Leu Arg Leu Val Phe Val Leu His Ala Thr Trp Cys Val Asn Ser
                180                 185                 190

Ala Ala His Lys Phe Gly Tyr Arg Pro Tyr Asp Ser Arg Ile Thr Pro
            195                 200                 205

Arg Asn Asn Trp Leu Val Ala Leu Val Thr Phe Gly Glu Gly Trp His
        210                 215                 220

Asn Phe His His Thr Phe Pro Tyr Asp Tyr Arg Asn Ala Glu Lys Trp
225                 230                 235                 240

Lys Trp Glu Tyr Asp Leu Thr Lys
                245

<210> SEQ ID NO 5
<211> LENGTH: 248
<212> TYPE: PRT
<213> ORGANISM: Artificial Sequence
<220> FEATURE:
<223> OTHER INFORMATION: conserved binding motif
<221> NAME/KEY: VARIANT
<222> LOCATION: (1)...(248)
<223> OTHER INFORMATION: Xaa = Any Amino Acid

<400> SEQUENCE: 5

His Xaa Xaa Xaa Xaa His Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa His
            35                  40                  45

Xaa Xaa Xaa His His Xaa Xaa Xaa Xaa Xaa Xaa Xaa Xaa Xaa Xaa
        50                  55                  60
```

```
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                     85                  90                  95

Xaa Xaa Xaa Xaa Xaa Xaa Xaa Xaa Xaa Xaa Xaa Xaa Xaa Xaa Xaa Xaa
                    100                 105                 110

Xaa Xaa Xaa Xaa Xaa Xaa Xaa Xaa Xaa Xaa Xaa Xaa Xaa Xaa Xaa Xaa
                115                 120                 125

Xaa Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                    165                 170                 175

Xaa Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa His Xaa Xaa Xaa His His
                245
```

<210> SEQ ID NO 6
<211> LENGTH: 15
<212> TYPE: PRT
<213> ORGANISM: Artificial Sequence
<220> FEATURE:
<223> OTHER INFORMATION: motif
<221> NAME/KEY: VARIANT
<222> LOCATION: 4, 7
<223> OTHER INFORMATION: Xaa = Phe or Tyr
<221> NAME/KEY: VARIANT
<222> LOCATION: 3, 10, 13
<223> OTHER INFORMATION: Xaa = Any Amino Acid

<400> SEQUENCE: 6

```
Gly Glu Xaa Xaa His Asn Xaa His His Xaa Phe Pro Xaa Asp Tyr
 1               5                  10                  15
```

<210> SEQ ID NO 7
<211> LENGTH: 359
<212> TYPE: PRT
<213> ORGANISM: Homo sapiens

<400> SEQUENCE: 7

```
Met Pro Ala His Leu Leu Gln Asp Asp Ile Ser Ser Ser Tyr Thr Thr
 1               5                  10                  15

Thr Thr Thr Ile Thr Ala Pro Pro Ser Arg Val Leu Gln Asn Gly Gly
                20                  25                  30

Asp Lys Leu Glu Thr Met Pro Leu Tyr Leu Glu Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
 65                  70                  75                  80
```

-continued

```
Leu Leu His Leu Gly Ala Leu Tyr Gly Ile Thr Leu Ile Pro Thr Cys
                 85                  90                  95

Lys Phe Tyr Thr Trp Leu Trp Gly Val Phe Tyr Phe Val Ser Ala
            100                 105                 110

Leu Gly Ile Thr Ala Gly Ala His Arg Leu Trp Ser His Arg Ser Tyr
            115                 120                 125

Lys Ala Arg Leu Pro Leu Arg Leu Phe Leu Ile Ile Ala Asn Thr Met
130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
                180                 185                 190

Val Lys Glu Lys Gly Ser Thr Leu Asp Leu Ser Asp Leu Glu Ala Glu
                195                 200                 205

Lys Leu Val Met Phe Gln Arg Arg Tyr Tyr Lys Pro Gly Leu Leu Leu
            210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
                260                 265                 270

Tyr Arg Pro Tyr Asp Lys Asn Ile Ser Pro Arg Glu Asn Ile Leu Val
            275                 280                 285

Ser Leu Gly Ala Val Gly Glu Gly Phe His Asn Tyr His His Ser Phe
            290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                325                 330                 335

Lys Lys Val Ser Lys Ala Ala Ile Leu Ala Arg Ile Lys Arg Thr Gly
                340                 345                 350

Asp Gly Asn Tyr Lys Ser Gly
            355

<210> SEQ ID NO 8
<211> LENGTH: 358
<212> TYPE: PRT
<213> ORGANISM: Rattus norvegicus

<400> SEQUENCE: 8

Met Pro Ala His Met Leu Gln Glu Ile Ser Ser Tyr Thr Thr Thr
  1               5                  10                  15

Thr Thr Ile Thr Glu Pro Pro Ser Gly Asn Leu Gln Asn Gly Arg Glu
             20                  25                  30

Lys Met Lys Lys Val Pro Leu Tyr Leu Glu Glu Asp Ile Arg Pro Glu
             35                  40                  45

Met Arg Glu Asp Ile His Asp Pro Ser Tyr Gln Asp Glu Glu Gly Pro
     50                  55                  60

Pro Pro Lys Leu Glu Tyr Val Trp Arg Asn Ile Ile Leu Met Ala Leu
 65                  70                  75                  80

Leu His Val Gly Ala Leu Tyr Gly Ile Thr Leu Ile Pro Ser Ser Lys
                 85                  90                  95
```

```
Val Tyr Thr Leu Leu Trp Gly Ile Phe Tyr Leu Ile Ser Ala Leu
            100                 105                 110

Gly Ile Thr Ala Gly Ala His Arg Leu Trp Ser His Arg Thr Tyr Lys
            115                 120                 125

Ala Arg Leu Pro Leu Arg Ile Phe Leu Ile Ile Ala Asn Thr Met Ala
130                 135                 140

Phe Gln Asn Asp Val Tyr Glu Trp Ala Arg Asp His Arg Ala His His
145                 150                 155                 160

Lys Phe Ser Glu Thr His Ala Asp Pro His Asn Ser Arg Arg Gly Phe
                165                 170                 175

Phe Phe Ser His Val Gly Trp Leu Leu Val Arg Lys His Pro Ala Val
                180                 185                 190

Lys Glu Lys Gly Gly Lys Leu Asp Met Ser Asp Leu Lys Ala Glu Lys
                195                 200                 205

Leu Val Met Phe Gln Arg Arg Tyr Tyr Lys Pro Gly Leu Leu Leu Met
            210                 215                 220

Cys Phe Ile Leu Pro Thr Leu Val Pro Trp Tyr Cys Trp Gly Glu Thr
225                 230                 235                 240

Phe Leu His Ser Leu Phe Val Ser Thr Phe Leu Arg Tyr Thr Leu Val
                245                 250                 255

Leu Asn Ala Thr Trp Leu Val Asn Ser Ala Ala His Leu Tyr Gly Tyr
            260                 265                 270

Arg Pro Tyr Asp Lys Asn Ile Gln Ser Arg Glu Asn Ile Leu Val Ser
            275                 280                 285

Leu Gly Ser Val Gly Glu Gly Phe His Asn Tyr His His Ala Phe Pro
    290                 295                 300

Tyr Asp Tyr Ser Ala Ser Glu Tyr Arg Trp His Ile Asn Phe Thr Thr
305                 310                 315                 320

Phe Phe Ile Asp Cys Met Ala Ala Leu Gly Leu Ala Tyr Asp Arg Lys
                325                 330                 335

Lys Val Ser Lys Ala Ala Val Leu Ala Arg Ile Lys Arg Thr Gly Asp
                340                 345                 350

Gly Ser His Lys Ser Ser
        355

<210> SEQ ID NO 9
<211> LENGTH: 357
<212> TYPE: PRT
<213> ORGANISM: Gallus gallus

<400> SEQUENCE: 9

Met Pro Ala His Leu Leu Gln Glu Glu Phe Ser Ser Ala Ser Ser
 1               5                  10                  15

Thr Thr Thr Val Thr Ser Arg Val Thr Lys Asn Gly Asn Val Ile Met
                20                  25                  30

Glu Lys Asp Leu Leu Asn His Asp Val Ala Ala Glu Arg Gly Met
            35                  40                  45

Val Asp Asp Leu Phe Asp Glu Thr Tyr Arg Glu Lys Glu Gly Pro Lys
    50                  55                  60

Pro Pro Leu Arg Tyr Val Trp Arg Asn Ile Ile Leu Met Ser Leu Leu
65                  70                  75                  80

His Leu Gly Ala Ile Ile Gly Leu Thr Leu Ile Pro Ser Ala Lys Ile
                85                  90                  95

Gln Thr Leu Ala Trp Ala Ile Leu Cys Phe Val Leu Ser Ala Leu Gly
            100                 105                 110
```

-continued

```
Ile Thr Ala Gly Ser His Arg Leu Trp Ser His Arg Ser Tyr Lys Ala
        115                 120                 125

Thr Leu Pro Leu Arg Ile Phe Leu Thr Ile Ala Asn Ser Met Ala Phe
        130                 135                 140

Gln Asn Asp Ile Tyr Glu Trp Ala Arg Asp His Arg Val His His Lys
145                 150                 155                 160

Phe Ser Glu Thr His Ala Asp Pro His Asn Ala Met Arg Gly Tyr Phe
                165                 170                 175

Phe Ser His Met Ala Trp Leu Leu Val Arg Lys His Pro Asp Val Ile
                180                 185                 190

Glu Lys Gly Gln Lys Leu Asp Leu Ser Asp Leu Lys Ala Asp Lys Val
        195                 200                 205

Val Met Phe Gln Arg Arg Tyr Tyr Lys Pro Ser Val Val Leu Leu Cys
        210                 215                 220

Phe Thr Leu Pro Thr Leu Val Pro Trp Tyr Phe Trp Asp Glu Ser Ile
225                 230                 235                 240

Ile Ile Ser Phe Phe Ile Pro Ala Ile Leu Arg Tyr Thr Leu Gly Leu
                245                 250                 255

Asn Ala Thr Trp Leu Val Asn Ser Ala Ala His Met Phe Gly Asn Arg
                260                 265                 270

Pro Tyr Asp Gln Asn Ile Asn Pro Arg Glu Asn Pro Leu Val Ser Val
        275                 280                 285

Gly Ala Leu Gly Glu Gly Phe His Asn Tyr His His Thr Phe Pro Tyr
        290                 295                 300

Asp Tyr Ser Thr Ser Glu Phe Gly Trp Arg Phe Asn Leu Thr Thr Ala
305                 310                 315                 320

Phe Ile Asp Leu Met Cys Leu Leu Gly Leu Ala Ser Asp Arg Lys Lys
                325                 330                 335

Val Ser Lys Glu Val Ile Leu Ala Arg Lys Met Arg Thr Gly Asp Gly
                340                 345                 350

Ser His Lys Ser Gly
        355
```

25934, A NOVEL FATTY ACID DESATURASE AND USES THEREFOR

RELATED APPLICATIONS

This application claims priority to U.S. provisional application No. 60/187,455 filed on Mar. 7, 2000, the contents of which are incorporated herein by reference.

BACKGROUND OF THE INVENTION

Fatty acid desaturases are critical regulatory enzymes of unsaturated fatty acid biosynthesis and catalyze the conversion of a single bond between two carbon atoms (C—C) to a double bond (C=C) in a fatty acyl chain. The resultant double bond is often referred to as an unsaturated bond. Eukaryotic fatty acid desaturases, typically, are iron-containing enzymes that catalyze the NAD-(P)H and $O_2$-dependent introduction of double bonds into methylene-interrupted fatty acid chains. Examination of the deduced amino acid sequence from mammals, fungi, insects, higher plants and cyanobacteria has revealed three regions of conserved primary sequence containing HX(3 or 4)H, HX(2 or 3), and HX(2 or 3)HH. This motif is also present in the bacterial membrane enzymes alkaline hydroxylase (omega-hydroxylase) and xylene monooxygenase.

There are three types of eukaryotic fatty acid desaturases, acyl-CoA, acyl-ACP, and acyl-lipid desaturases (Ntambi et al., Biochem. and Biophys. Res. Com. 266:1–4, 1999). In plants and cyanobacteria, acyl-lipid desaturases catalyzing most desaturation reactions and introduce unsaturated bonds into fatty acids that are in a lipid-bound form. Acyl-ACP desaturases are present in the plastids of plant cells and insert a double bond into fatty acids that are bound to acyl carrier protein (ACP). In animals, yeast and fungal cells, Acyl-CoA introduce unsaturated bonds into fatty acids that are bound to coenzyme A (CoA). A gene cloned from this family is stearoyl-CoA desaturase and this gene has been identified in many organisms including mice, rats, humans, yeast, ovines, and hamsters.

Fatty acid desaturases can introduce an unsaturated bond at a specific position in a fatty acyl chain, for example, at the Δ6, Δ9, or Δ12 position. Desaturases are typically integral membrane proteins induced in the endoplasmic reticulum by dietary manipulations and then rapidly degraded (Ozols, J. (1997) MBC Vol. 8 (11): 2281–2290). Unsaturated fatty acids can be formed from a variety of fatty acids including palmitate and stearate resulting in the formation of unsaturated fatty acids palmitoleate (16:1), and oleate (18:1).

In mammals, the rate limiting step in the biosynthesis of monounsaturated fatty acids is the insertion of an unsaturated bond by stearoyl-CoA desaturase (SCD) in the Δ9 position of the fatty acid. SCD preferentially catalyzes the synthesis of oleic acid. Oleate enriched low density lipoprotein (LDL) exhibits increased affinity for the vessel wall, and is therefore pro-atherogenic (Rudel, L. L. et al. (1997) J. Clin. Invest. 1:100(1):74–83). SCD involvement in generating atherogenic LDL variants and in regulating triglyceride synthesis is further supported by the finding that polyunsaturated fatty acids (PUFA), which protect against atherosclerosis, negatively regulate the expression of the SCD gene (Rudel, L L et al. (1995) Atheroscler. Thromb. Vasc. Biol. 15(12):2101–10; Ntambi, J M (1999) J. Lipid Res. 40(9):1549–58). Moreover, a mouse deficient for SCD exhibits significant reduction in triglycerides (Miyazaki, M. et al. (2000) J. Biol. Chem, in press).

Unsaturated fatty acids play an important role in normal and diseased organisms. For example, the degree of fatty acid unsaturation in cell membrane lipids determines membrane fluidity. Moreover, the production of monounsaturated fatty acids, which once complexed with lipoproteins such as LDL, show increased affinity for the vessels wall has profound implications for cardiovascular disorders caused by aberrant fatty acid metabolism. Examples of such disorders include atherosclerosis, hypertriglyceridemia, hypercholesterolemia, hyperlipidemia, among others.

SUMMARY OF THE INVENTION

The present invention is based, in part, on the discovery of a novel fatty acid desaturase, referred to herein as "25934". The nucleotide sequence of a cDNA encoding 25934 is shown in SEQ ID NO:1, and the amino acid sequence of a 25934 polypeptide is shown in SEQ ID NO:2. In addition, the nucleotide sequences of the coding region are depicted in SEQ ID NO:3.

Accordingly, in one aspect, the invention features a nucleic acid molecule which encodes a 25934 protein or polypeptide, e.g., a biologically active portion of the 25934 protein. In a preferred embodiment the isolated nucleic acid molecule encodes a polypeptide having the amino acid sequence of SEQ ID NO:2. In other embodiments, the invention provides isolated 25934 nucleic acid molecules having the nucleotide sequence shown in SEQ ID NO:1, SEQ ID NO:3, or the sequence of the DNA insert of the plasmid deposited with ATCC Accession Number 2167. In still other embodiments, the invention provides nucleic acid molecules that are substantially identical (e.g., naturally occurring allelic variants) to the nucleotide sequence shown in SEQ ID NO:1, SEQ ID NO:3, or the sequence of the DNA insert of the plasmid deposited with ATCC Accession Number 2167. In other embodiments, the invention provides a nucleic acid molecule which hybridizes under stringent hybridization conditions to a nucleic acid molecule comprising the nucleotide sequence of SEQ ID NO:1 or 3, or the sequence of the DNA insert of the plasmid deposited with ATCC Accession Number 2167, wherein the nucleic acid encodes a full length 25934 protein or an active fragment thereof.

In a related aspect, the invention further provides nucleic acid constructs which include a 25934 nucleic acid molecule described herein. In certain embodiments, the nucleic acid molecules of the invention are operatively linked to native or heterologous regulatory sequences. Also included, are vectors and host cells containing the 25934 nucleic acid molecules of the invention e.g., vectors and host cells suitable for producing 25934 nucleic acid molecules and polypeptides.

In another related aspect, the invention provides nucleic acid fragments suitable as primers or hybridization probes for the detection of 25934-encoding nucleic acids.

In still another related aspect, isolated nucleic acid molecules that are antisense to a 25934 encoding nucleic acid molecule are provided.

In another aspect, the invention features, 25934 polypeptides, and biologically active or antigenic fragments thereof that are useful, e.g., as reagents or targets in assays applicable to treatment and diagnosis of 25934 mediated or related disorders, e.g., a cardiovascular disorder. In another embodiment, the invention provides 25934 polypeptides having a 25934 activity. Preferred polypeptides are 25934 proteins including at least one desaturase domain, and, preferably, having a 25934 activity, e.g., a 25934 activity as described herein.

In other embodiments, the invention provides 25934 polypeptides, e.g., a 25934 polypeptide having the amino acid sequence shown in SEQ ID NO:2; the amino acid sequence encoded by the cDNA insert of the plasmid deposited with ATCC Accession Number 2167; an amino acid sequence that is substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or 3, or the sequence of the DNA insert of the plasmid deposited with ATCC Accession Number 2167, wherein the nucleic acid encodes a full length 25934 protein or an active fragment thereof.

In a related aspect, the invention further provides nucleic acid constructs which include a 25934 nucleic acid molecule described herein.

In a related aspect, the invention provides 25934 polypeptides or fragments operatively linked to non-25934 polypeptides to form fusion proteins.

In another aspect, the invention features antibodies and antigen-binding fragments thereof, that react with, or more preferably specifically bind 25934 polypeptides.

In another aspect, the invention provides methods of screening for compounds that modulate the expression or activity of the 25934 polypeptides or nucleic acids.

In still another aspect, the invention provides a process for modulating 25934 polypeptide or nucleic acid expression or activity, e.g. using the screened compounds. In certain embodiments, the methods involve treatment or prophylaxis of conditions related to activity or expression of the 25934 polypeptides or nucleic acids, such as cardiovascular, neurological, metabolic, reproductive (e.g., ovarian), renal and hepatic disorders.

Examples of cardiovascular disorders include e.g., atherosclerosis, thrombosis, heart failure, ischemic heart disease, angina pectoris, myocardial infarction, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stet, stent, synthetic or natural excision grafts, indwelling catheter, valve or other implantable devices.

In a preferred embodiment, the cardiovascular disorder is caused by aberrant fatty acid metabolism. Examples of disorders involving aberrant fatty acid metabolism include, but are not limited to, atherosclerosis, arteriolosclerosis, hypertriglyceridemia, obesity, diabetes, hypercholesterolemia, xanthomatosis, and hyperlipidemia. Most preferable, the disorder is atherosclerosis.

In the cardiovascular applications, the agent is administered alone or in combination with a cholesterol lowering agent. Examples of cholesterol lowering agents include bile acid sequestering resins (e.g. colestipol hydrochloride or cholestyramine), fibric acid derivatives (e.g. clofibrate, fenofibrate, or gemfibrozil), thiazolidenediones (e.g. troglitazone), or hydroxymethylglutaryl coenzyme A reductase (HMG-CoA reductase) inhibitors (e.g. statins, such as fluvastatin sodium, lovastatin, pravastatin sodium, or simvastatin), an ApoAII-lowering agent, a VLDL lowering agent, an ApoAI-stimulating agent, as well as inhibitors of, nicotinic acid, niacin, or probucol. Preferred cholesterol lowering agents include inhibitors of HMG-CoA reductase (e.g., statins), nicotinic acid, and niacin.

The cholesterol lowering agent can be administered prior to, at the same time, or after administration of the agent, in single or multiple administration schedules. For example, the cholesterol lowering agent and the agents of the invention can be administered continually over a preselected period of time, or administered in a series of spaced doses, i.e., intermittently, for a period of time.

In a preferred embodiments, the agent, alone or in combination with the cholesterol lowering agent, inhibit (block or reduce) atherosclerotic lesion formation or development, e.g., so as to inhibit lipid accumulation, increase plaque stability or promote lesion regression.

In still another aspect, the invention features a method of modulating (e.g., enhancing or inhibiting) fatty acid metabolism, in a subject. The method includes administering to the subject an agent that modulates the activity or expression of a 25934 polypeptide or nucleic acid, in an amount effective to modulate the conversion of saturated fatty acids to unsaturated fatty acids, e.g., monounsaturated fatty acids.

In a preferred embodiment, the 25934 polypeptide has an amino acid sequence identical to, or substantially identical to, SEQ ID NO:2. In other embodiments, the 25934 polypeptide is a fragment of at least 15, 20, 50, 100, 150, 200, 250, 300 or more contiguous amino acids of SEQ ID NO:2.

In a preferred embodiment, the 25934 nucleic acid has a nucleotide sequence identical to, or substantially identical to, SEQ ID NO:1 or 3. In other embodiments, the 25934 nucleic acid is a fragment of at least 50, 100, 150, 200, 250, 300, 350, 400, 450, 500, 600, 700, 800, 900 or more contiguous nucleotides of SEQ ID NO:1 or 3.

In a preferred embodiment, the agent modulates, e.g., decreases or blocks, desaturase activity or expression. For example, the agent (e.g., a polyunsaturated fatty acid, or nicotinic acid or niacin) may negatively regulate 25934 protein expression.

In a preferred embodiment, the agent modulates (e.g., decreases or increases) the activity or expression of a 25934 polypeptide or nucleic acid such that modulation of one or more of: lipoprotein composition, lipid (e.g., triglyceride) levels, apolipoprotein B, total cholesterol, or lipoprotein (a), occurs. For example, the agent can decrease low density lipoprotein (LDL)-cholesterol levels, and/or lipid (e.g., triglyceride) levels. Preferably, the agent can also increase high-density lipoprotein (HDL)-cholesterol levels.

In a preferred embodiment, the agent modulates (e.g., increases or decreases) expression of the 25934 nucleic acid by, e.g., modulating transcription, mRNA stability, etc.

In preferred embodiments, the agent is a peptide, a phosphopeptide, a small molecule, e.g., a member of a combinatorial or natural product library, or an antibody, or any combination thereof.

In additional preferred embodiments, the agent is an antisense, a ribozyme, or a triple helix molecule, or a 25934 nucleic acid or a fragment thereof, or any combination thereof.

In a preferred embodiment, the subject is a patient undergoing a therapeutic or prophylactic protocol. Preferably, the subject is a human suffering from, or at risk of a cardiovascular disease, e.g., atherosclerosis, thrombosis, heart failure, ischemic heart disease, angina pectoris, myocardial infarction, sudden cardiac death, hypertensive heart disease; non-coronary vessel disease, such as arteriolosclerosis, small vessel disease, nephropathy, hypertriglyceridemia, obesity, diabetes, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stet, stent, synthetic or natural excision grafts, indwelling catheter, valve or other implantable devices.

In a preferred embodiment, the subject is a human suffering from, or at risk of a disorder involving aberrant fatty acid metabolism. Examples of such disorders include, but are not limited to, atherosclerosis, arteriolosclerosis, hypertriglyceridemia, obesity, diabetes, hypercholesterolemia, xanthomatosis and hyperlipidemia. Most preferable, the disorder is atherosclerosis.

In other embodiments, the subject is a non-human animal, e.g., an experimental animal.

In a preferred embodiment, the agent is administered alone or in combination with a cholesterol lowering agent. Examples of cholesterol lowering agents include bile acid sequestering resins (e.g. colestipol hydrochloride or cholestyramine), fibric acid derivatives (e.g. clofibrate, fenofibrate, or gemfibrozil), thiazolidenediones (e.g. troglitazone), or hydroxymethylglutaryl coenzyme A reductase (HMG-CoA reductase) inhibitors (e.g. statins, such as fluvastatin sodium, lovastatin, pravastatin sodium, or simvastatin), an ApoAII-lowering agent, a VLDL lowering agent, an ApoAI-stimulating agent, as well as inhibitors of, nicotinic acid, niacin, or probucol. Preferred cholesterol lowering agents include inhibitors of HMG-CoA reductase (e.g., statins), nicotinic acid, and niacin.

The cholesterol lowering agent can be administered prior to, at the same time, or after administration of the agent, in single or multiple administration schedules. For example, the cholesterol lowering agent and the agents of the invention can be administered continually over a preselected period of time, or administered in a series of spaced doses, i.e., intermittently, for a period of time.

In a preferred embodiment, the agent, alone or in combination with the cholesterol lowering agent, inhibits (blocks or reduces) atherosclerotic lesion formation or development, e.g., so as to inhibit lipid accumulation, increase plaque stability or promote lesion regression.

In a preferred embodiment, the agent, administered alone or in combination with the cholesterol lowering agent, results in a favorable plasma lipid profile (e.g., increased HDL and/or reduced LDL).

In yet another aspect, the invention features a method of treating or preventing a cardiovascular disorder (e.g., atherosclerosis), in a subject. The method includes administering to the subject an agent that modulates the activity or expression of a 25934 polypeptide or nucleic acid, in an amount effective to treat or prevent the cardiovascular disorder.

In a preferred embodiment, the 25934 polypeptide has an amino acid sequence identical to, or substantially identical to, SEQ ID NO:2. In other embodiments, the 25934 polypeptide is a fragment of at least 15, 20, 50, 100, 150, 200, 250, 300 or more contiguous amino acids of SEQ ID NO:2.

In a preferred embodiment, the 25934 nucleic acid has a nucleotide sequence identical to, or substantially identical to, SEQ ID NO:1 or 3. In other embodiments, the 25934 nucleic acid is a fragment of at least 50, 100, 150, 200, 250, 300, 350, 400, 450, 500, 600, 700, 800, 900 or more contiguous nucleotides of SEQ ID NO:1 or 3.

In a preferred embodiment, the agent modulates, e.g., decreases or blocks, desaturase activity or expression. For example, the agent (e.g., a polyunsaturated fatty acid, or nicotinic acid or niacin) may negatively regulate 25934 protein expression.

In a preferred embodiment, the agent modulates (e.g., decreases or increases) the activity or expression of a 25934 polypeptide or nucleic acid such that modulation of one or more of: lipoprotein composition, lipid (e.g., triglyceride) levels, apolipoprotein B, total cholesterol, or lipoprotein (a), occurs. For example, the agent can decrease low density lipoprotein (LDL)-cholesterol levels, and/or lipid (e.g., triglyceride) levels. Preferably, the agent can also increase high-density lipoprotein (HDL)-cholesterol levels.

In a preferred embodiment, the agent modulates (e.g., increases or decreases) expression of the 25934 nucleic acid by, e.g., modulating transcription, mRNA stability, etc.

In preferred embodiments, the agent is a peptide, a phosphopeptide, a small molecule, e.g., a member of a combinatorial or natural product library, or an antibody, or any combination thereof.

In additional preferred embodiments, the agent is an antisense, a ribozyme, or a triple helix molecule, or a 25934 nucleic acid or a fragment thereof, or any combination thereof.

In a preferred embodiment, the subject is a patient undergoing a therapeutic or prophylactic protocol. Preferably, the subject is a human suffering from, or at risk of a cardiovascular disease, e.g., atherosclerosis, thrombosis, heart failure, ischemic heart disease, angina pectoris, myocardial infarction, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stet, stent, synthetic or natural excision grafts, indwelling catheter, valve or other implantable devices.

In a preferred embodiment, the subject is a human suffering from, or at risk of a disorder involving aberrant fatty acid metabolism. Examples of such disorders include, but are not limited to, atherosclerosis, arteriolosclerosis, hypertriglyceridemia, obesity, diabetes, hypercholesterolemia, xanthomatosis and hyperlipidemia. Most preferable, the disorder is atherosclerosis.

In other embodiments, the subject is a non-human animal, e.g., an experimental animal.

In a preferred embodiment, the agent is administered alone or in combination with a cholesterol lowering agent. Examples of cholesterol lowering agents include bile acid sequestering resins (e.g. colestipol hydrochloride or cholestyramine), fibric acid derivatives (e.g. clofibrate, fenofibrate, or gemfibrozil), thiazolidenediones (e.g. troglitazone), or hydroxymethylglutaryl coenzyme A reductase (HMG-CoA reductase) inhibitors (e.g. statins, such as fluvastatin sodium, lovastatin, pravastatin sodium, or simvastatin), an ApoAII-lowering agent, a VLDL lowering agent, an ApoAI-stimulating agent, as well as inhibitors of, nicotinic acid, niacin, or probucol. Preferred cholesterol lowering agents include inhibitors of HMG-CoA reductase (e.g., statins), nicotinic acid, and niacin.

The cholesterol lowering agent can be administered prior to, at the same time, or after administration of the agent in single or multiple administration schedules. For example, the cholesterol lowering agent and the agents of the invention can be administered continually over a preselected period of time, or administered in a series of spaced doses, i.e., intermittently, for a period of time as a therapeutic or preventative measure.

In a preferred embodiment, the agent, alone or in combination with the cholesterol lowering agent, inhibits (blocks or reduces) atherosclerotic lesion formation or development, e.g., so as to inhibit lipid accumulation, increase plaque stability or promote lesion regression.

In a preferred embodiment, the agent, administered alone or in combination with the cholesterol lowering agent, results in a favorable plasma lipid profile (e.g., increased HDL and/or reduced LDL).

The invention also features a method of diagnosing a disorder, e.g., a cardiovascular disorder (e.g., atherosclerosis), in a subject. The method includes evaluating the expression or activity of a 25934 nucleic acid or a 25934 polypeptide, such that, a difference in the level of 25934 nucleic acid or 25934 polypeptide relative to a normal subject or a cohort of normal subjects is indicative of the disorder. Because 25934 is regulated by Niacin (a clinically used therapeutic), 25934 levels and/or activity may be considered a marker for Niacin activity and or efficacy.

In a preferred embodiment, the subject is a human.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 25934 nucleic acid or polypeptide, such that a signal is generated relative to the level of activity or expression of the 25934 nucleic acid or polypeptide.

In a preferred embodiment, the disorder is a cardiovascular disorder, e.g., a cardiovascular disorder as described herein.

In a preferred embodiment, the disorder is atherosclerosis.

The invention also provides assays for determining the activity of or the presence or absence of 25934 polypeptides or nucleic acid molecules in a biological sample, including for disease diagnosis.

In a further aspect, the invention provides assays for determining the presence or absence of a genetic alteration in a 25934 polypeptide or nucleic acid molecule, including for disease diagnosis, predicting triglyceride levels, predicting response to Niacin, and predicting a response to triglyceride therapy.

In yet another aspect, the invention features a method for identifying an agent, e.g., a compound, which modulates the activity of a 25934 polypeptide, e.g., a 25934 polypeptide as described herein, or the expression of a 25934 nucleic acid, e.g., a 25934 nucleic acid as described herein, including contacting the 25934 polypeptide or nucleic acid with a test agent (e.g., a test compound); and determining the effect of the test compound on the activity of the polypeptide or nucleic acid to thereby identify a compound which modulates the activity of the polypeptide or nucleic acid. Such agents are useful for treating or preventing a 25934-mediated disorders, e.g., cardiovascular disorders (e.g., atherosclerosis) or metabolic disorders (e.g., obesity or diabetes).

In a preferred embodiment, the contacting step occurs in vitro or ex vivo. For example, a sample, e.g., a blood sample, is obtained from the subject.

In a preferred embodiment, the contacting step occurs in vivo. For example, by administering to the subject a detectably labeled agent that interacts with the 25934 nucleic acid or polypeptide, such that a signal is generated relative to the level of activity or expression of the 25934 nucleic acid or polypeptide.

In a preferred embodiment, the activity of the 25934 polypeptide is protein desaturase activity, e.g., catalyzing the conversion of saturated fatty acids to unsaturated fatty acids. In such embodiment, the 25934 polypeptide is contacted with a saturated fatty acid, e.g., oleic acid, palmitate and stearate.

In a preferred embodiment, the agent is an inhibitor (partial or complete inhibitor) of 25934 polypeptide activity or expression.

In a preferred embodiment, the agent modulates one or more of: lipoprotein composition, lipid (e.g., triglyceride) levels, LDL, HDL, apolipoprotein B, total cholesterol, or lipoprotein (a). For example, the agent can decrease low density lipoprotein (LDL)-cholesterol levels, and/or lipid (e.g., triglyceride) levels. Preferably, the agent can also increase high-density lipoprotein (HDL)-cholesterol levels.

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, a triple helix molecule, or a 25934 nucleic acid, or any combination thereof.

Other features and advantages of the invention will be apparent from the following detailed description, and from the claims.

BRIEF DESCRIPTION OF THE DRAWINGS

FIGS. 1A–B depict a cDNA sequence (SEQ ID NO:1) and predicted amino acid sequence (SEQ ID NO:2) of human 25934. The methionine-initiated open reading frame of human 25934 (without the 5' and 3' untranslated regions) which occurs at nucleotide 403 through 1392 of SEQ ID NO:1 (shown also as coding sequence (SEQ ID NO:3).

FIG. 3 depicts an alignment of the desaturase domain of human 25934 with a consensus amino acid sequence derived from a hidden Markov model using PFAM. The upper sequence is the consensus amino acid sequence (SEQ ID NO:4), while the lower amino acid sequence corresponds to amino acids 51 to 295 of SEQ ID NO:2.

FIG. 8 is a multiple sequence alignment of the 25934 amino acid sequence with the human (SEQ ID NO:7), rat (SEQ ID NO:8), and chicken (SEQ ID NO:9) delta-9 desaturase proteins. A comparison of the full length amino acid sequence revealed 63.6%, 58.4%, and 58.4% identity between the 25934 amino acid sequence and the chicken, human and rat amino acid sequences, respectively.

DETAILED DESCRIPTION OF THE INVENTION

Figure 2:
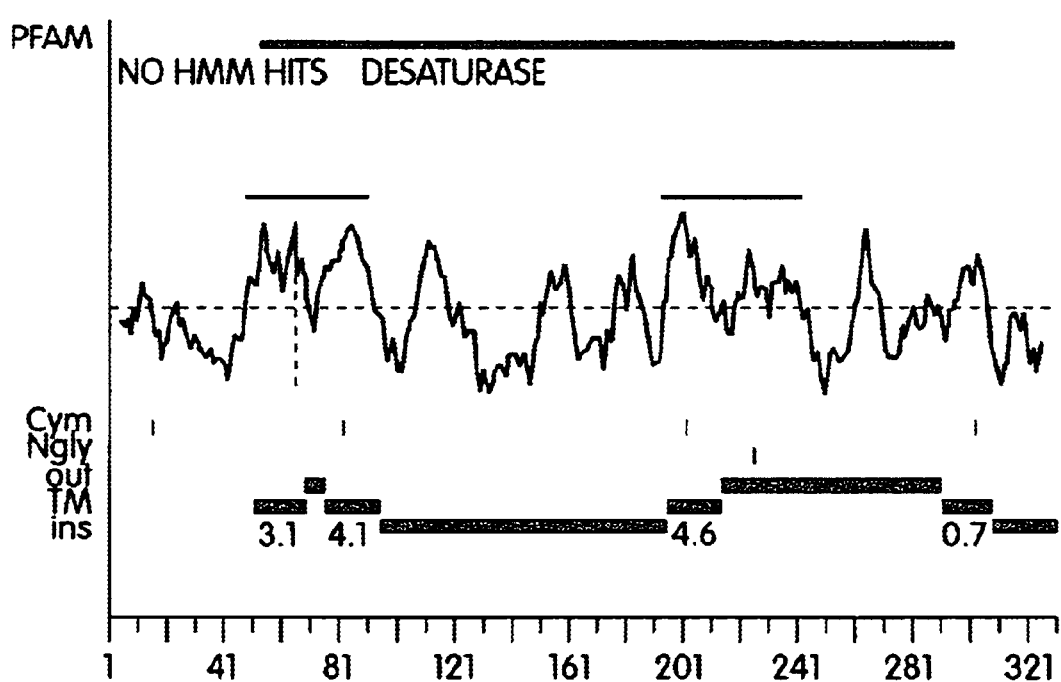
FIG. 2 depicts a hydropathy plot of human 25934. Relative hydrophobic residues are shown above the dashed horizontal line, and relative hydrophilic residues are below the dashed horizontal line. The cysteine residues (cys) and an N-glycosylation site are indicated by short vertical lines just below the hydropathy trace. The transmembrane regions are indicated by horizontal lines above the hydropathy trace. The numbers corresponding to the amino acid sequence of human 25934 are indicated. Polypeptides of the invention include 25934 fragments which include: all or part of a hydrophobic sequence (a sequence above the dashed line, e.g., all or part of the sequence from about residue 71 to about residue 91 of SEQ ID NO:2; all or part of a hydrophilic fragment (e.g., a fragment below the dashed line). Other fragments include a cysteine or a glycosylation site.

The human 25934 sequence (FIGS. 1A–B; SEQ ID NO:1), which is approximately 1512 nucleotides long including untranslated regions, contains a predicted methionine-initiated coding sequence of about 990 nucleotides (nucleotides 403–1392 of SEQ ID NO:1; SEQ ID NO:3). The coding sequence encodes a 330 amino acid protein (SEQ ID NO:2).

Human 25934 contains the following regions or other structural features: a desaturase domain located at about amino acid residues 51 to 295 of SEQ ID NO:2; two transmembrane regions at about amino acids 50–93 and 194–235 of SEQ ID NO:2; three cytoplasmic domains at about amino acids 1–49, 94–193, and 236–330 of SEQ ID NO:2; one predicted N-glycosylation site (PS00001) at about amino acids 233 to 236 of SEQ ID NO:2; one predicted cAmp and cGMP dependent protein kinase phosphorylation site (PS00004) at about amino acids 311 to 314 of SEQ ID NO:2; four predicted Protein Kinase C phosphorylation sites (PS00005) at about amino acids 98 to 100, 101 to 103, 255 to 257 and 308 to 310 of SEQ ID NO:2; two predicted Casein Kinase II phosphorylation sites (PS00006) located at about amino acids 138 to 141 and 283–286 of SEQ ID NO:2; four predicted N-myristoylation sites (PS00008) from about amino acids 23 to 28, 40 to 45, 59 to 64, and 88 to 93 of SEQ ID NO:2; one predicted amidation site (PS00009) from about amino acid 170 to 173 of SEQ ID NO:2; and one predicted fatty acid desaturase family 1 signature (PS00476) from about amino acid 268 to 282 of SEQ ID NO:2.

For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

A plasmid containing the nucleotide sequence encoding human 25934 was deposited with American Type Culture Collection (ATCC), 10801 University Boulevard, Manassas, Va. 20110-2209, on Jun. 27, 2000 and assigned Accession Number 2167. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The 25934 protein contains a significant number of structural characteristics in common with members of the desaturase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Based on sequence homology, 25934 polypeptide is predicted to be a member of the desaturase family of enzymes, specifically the stearoyl-Co desaturase family (SCD family, EC 1.14.99.5) (see FIGS. 3 and 8). These enzymes are structurally and functionally homologous to one another, and can convert a single bond to a double bond in a fatty acyl chain. SCD enzymes utilize oxygen and electrons from cytochrome $b_5$ for catalysis. Similar to other enzymes such as ribonucleotide reductases and methane monoxygenases, stearoyl-CoA desaturases can have a conserved iron binding motif which includes eight histidines (Shanklin et al. (1997) *Proc. Natl. Acad. Sci. USA* 94:2981–2986), "H-X(3-4)-H-X(7-41)-H-X(2-3)-H-H-X(61-189)-H-X(2-3)-H-H (SEQ ID NO:5)." The eight histidine residues common to desaturase family members are typically divided among three regions of the protein: region Ia (H-X(3-4)-H); region Ib (the first H-X(2-3)-H-H sequence); and region II (the second H-X(2-3)-H-H sequence) (Shanklin et al. (1994) *Biochemistry* 33:12787–94).

SCDs typically contain two or three long hydrophobic domains termed "transmembrane regions," each of which is capable of spanning the membrane two times (Shanklin et al. (1994) *Biochemistry* 33:12787–94). Because a transmembrane region is capable of traversing the membrane twice, amino acid residues flanking a transmembrane region reside on the same side of the membrane (Stukey et al. (1990) *J. Biol. Chem.* 265:20144–49). Thus, when region I (regions Ia and Ib) and region II are divided by a transmembrane region in a desaturase family member, the regions will typically reside on the same side of the membrane, e.g., the cytoplasmic face of the endoplasmic reticulum membrane.

A 25934 polypeptides include a "desaturase domain" or regions homologous with a "desaturase domain". As used herein, the term "desaturase domain" includes an amino acid sequence of about 25 to 600 amino acid residues in length and having a bit score for the alignment of the sequence to the fatty acid desaturase domain (HMM) of at least 50. Preferably, a desaturase domain includes at least about 50–500 amino acids, more preferably about 100–400 amino acid residues, or about 200–250 amino acids and has a bit score for the alignment of the sequence to the desaturase domain (HMM) of at least 60, 80, 100, 150, 200, 250, 300, 450, 500 or greater. An alignment of the desaturase domain (amino acids 51 to 295 of SEQ ID NO:2) of human 25934 with a consensus amino acid sequence derived from a hidden Markov model is depicted in FIG. 3.

In a preferred embodiment, 25934 polypeptide or protein has a "desaturase domain" or a region which includes at least about 50–500 amino acids, more preferably about 100–400 amino acid residues, or about 200–250 amino acid residues and has at least about 70% 80% 90% 95%, 99%, or 100% homology with a "desaturase domain," e.g., the desaturase domain of human 25934 (e.g., residues 51–295 of SEQ ID NO:2). Preferably, the desaturase domain of a 25934 polypeptide includes at least one, two, three, four, five, six, seven and preferably eight conserved histidines. Preferably, the histidines form an eight-histidine motif, which binds two iron atoms in the catalytic center. For example, a 25934 polypeptide contains histidine residues at about amino acids 94, 99, 131, 134, 135, 272, 275, and 276 of SEQ ID NO:2.

To identify the presence of a "desaturase" domain in a 25934 protein sequence, and make the determination that a polypeptide or protein of interest has a particular profile, the amino acid sequence of the protein can be searched against a database of HMMs (e.g., the Pfam database, release 2.1) using the default parameters sanger.ac.uk/Software/Pfam/HMM_search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "desaturase domain" domain in the amino acid sequence of human 25934 at about residues 51–295 of SEQ ID NO:2 (see FIGS. 1A–B).

A 25934 family member includes a desaturase domain and optionally also a fatty acid desaturase family 1 signature, i.e., a motif that matches the ProSite motif PS00476, "G-E-X-[FY]-H-N-[FY]-H-H-X-F-P-X-D-Y (SEQ ID NO:6)," e.g., the peptide sequence "GEGFH-NYHTFPFDY" located at about residues 268 to 282 of SEQ ID NO:2.

In one embodiment, a 25934 protein includes at least one, preferably two, transmembrane regions. As used herein, the term "transmembrane region" includes an amino acid sequence of about 20 amino acid residues in length that spans a phospholipid membrane, e.g., an endoplasmic reticulum membrane, twice. More preferably, a transmembrane region includes about at least 22, 24, 25, 30, 35, 40, 45, 50, 55, 60, 65, or 70 amino acid residues and spans a phospholipid membrane twice. Transmembrane regions are rich in hydrophobic residues, and typically have an a-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane regions are described in, for example, http://pfam.wustl.edu/cgi-bin/getdesc?name=7tm-1, and Zagotta W. N. et al, (1996) *Annual Rev. Neuronsci.* 19: 235–63, the contents of which are incorporated herein by reference.

In a preferred embodiment, a 25934 polypeptide or protein has at least one transmembrane region or a region which includes at least 20, 22, 24, 25, 30, 35, 40, 45, 50, 55, 60, 65, or 70 amino acid residues and has at least about 60%, 70% 80% 90% 95%, 99%, or 100% homology with a "transmembrane region," e.g., at least one transmembrane region of human 25934 (e.g., amino acid residues 50–93 or 194–235 of SEQ ID NO:2).

In one embodiment, a 25934 protein includes at least one cytoplasmic domain. When located at the N-terminal domain the cytoplasmic domain is referred to herein as an "N-terminal cytoplasmic domain". As used herein, an "N-terminal cytoplasmic domain" includes an amino acid sequence having about 1–200, preferably about 10–100, preferably about 20–90, more preferably about 30–80, more preferably about 35–70, more preferably about 40–60, or even more preferably about 45–55 amino acid residues in length and is located in the cytoplasm of a cell. The C-terminal amino acid residue of a "N-terminal cytoplasmic domain" is adjacent to an N-terminal amino acid residue of a transmembrane region in a 25934 protein. For example, an N-terminal cytoplasmic domain is located at about amino acid residues 1–49 of SEQ ID NO:2.

In a preferred embodiment, a 25934 polypeptide or protein has at least one N-terminal cytoplasmic domain or a region which includes at least about 5, preferably about 40–60, or even more preferably about 45–55 amino acid residues and has at least about 60%, 70% 80% 90% 95%, 99%, or 100% homology with an "N-terminal cytoplasmic domain," e.g., at least one N-terminal cytoplasmic domain of human 25934 (e.g., residues 1–49 of SEQ ID NO:2).

In another embodiment, a 25934 protein includes a "cytoplasmic loop" in the sequence of the protein. As used herein, a "cytoplasmic loop" includes an amino acid sequence having a length of at least about 10, preferably about 20–250, preferably about 30–150, more preferably about 80–120 amino acid residues and is located within the cytoplasm of a cell. Accordingly, the N-terminal amino acid residue of a "cytoplasmic loop" is adjacent to a C-terminal amino acid residue of a transmembrane region and the C-terminal residue of a "cytoplasmic loop" is adjacent to a N-terminal amino acid residue of a transmembrane region in a 25934 protein. For example, a cytoplasmic loop is found at about amino acid residues 94–193 of SEQ ID NO:2.

In a preferred embodiment, a 25934 polypeptide or protein has a cytoplasmic loop or a region which includes at least about 10, preferably about 20–250, preferably about 30–150, more preferably about 80–120 amino acid residues and has at least about 60%, 70% 80% 90% 95%, 99%, or 100% homology with an "cytoplasmic loop," e.g., the cytoplasmic loop of human 25934 (e.g., residues 94–193 of SEQ ID NO:2).

In another embodiment, a 25934 protein includes a "C-terminal cytoplasmic domain", also referred to herein as a C-terminal cytoplasmic tail, in the sequence of the protein.

As used herein, a "C-terminal cytoplasmic domain" includes an amino acid sequence having a length of at least about 30, preferably about 50–150, preferably about 60–200, more preferably about 80–110 amino acid residues and is located within the cytoplasm of a cell. Accordingly, the N-terminal amino acid residue of a "C-terminal cytoplasmic domain" is adjacent to a C-terminal amino acid residue of a transmembrane region in a 25934 protein. For example, a C-terminal cytoplasmic domain is found at about amino acid residues 236–330 of SEQ ID NO:2.

In a preferred embodiment, a 25934 polypeptide or protein has a C-terminal cytoplasmic domain or a region which includes at least about 30, preferably about 50–150, preferably about 60–200, more preferably about 80–110 amino acid residues and has at least about 60%, 70% 80% 90% 95%, 99%, or 100% homology with an "C-terminal cytoplasmic domain," e.g., the C-terminal cytoplasmic domain of human 25934 (e.g., residues 236–330 of SEQ ID NO:2).

As the 25934 polypeptides of the invention may modulate 25934-mediated activities, they may be useful as of for developing novel diagnostic and therapeutic agents for 25934-mediated or related disorders, as described below.

As used herein, a "25934 activity", "biological activity of 25934" or "functional activity of 25934", refers to an activity exerted by a 25934 protein, polypeptide or nucleic acid molecule on e.g., a 25934-responsive cell or on a 25934 substrate, e.g., a protein substrate, as determined in vivo or in vitro. In one embodiment, a 25934 activity is a direct activity, such as an association with a 25934 target molecule. A "target molecule" or "binding partner" is a molecule with which a 25934 protein binds or interacts in nature. In an exemplary embodiment, the binding partner is a fatty acid, e.g., myristic, palmitic or stearic acid. The 25934 proteins of the present invention can have one or more of the following activities: (1) catalyzing the formation of a double bond, preferably, at positions up to 9 carbons from the carboxyl end of a molecule, e.g., a fatty acid, such as a polyunsaturated fatty acid; (2) modulating the synthesis of monounsaturated fatty acids, e.g., modulating the synthesis of a fatty acid synthesized in an animal, e.g., oleic acid, palmitoyl- and stearoyl-CoA; (3) modulating the desaturation of a fatty acid, e.g., a polyunsaturated fatty acids; (4) modulating cellular lipid composition, e.g., modulating the ratio of saturated and unsaturated fatty acids; (5) modulating the energy state of adipocytes; (6) modulating membrane fluidity; (7) modulating lipid storage; (8) modulating proliferation and/or differentiation; (9) modulating lipoprotein (e.g., LDL) composition and/or concentration; (10) regulating triglyceride synthesis; (11) altering the HDL/LDL ration; or (12) modulating fatty acid metabolism.

Figure 7:
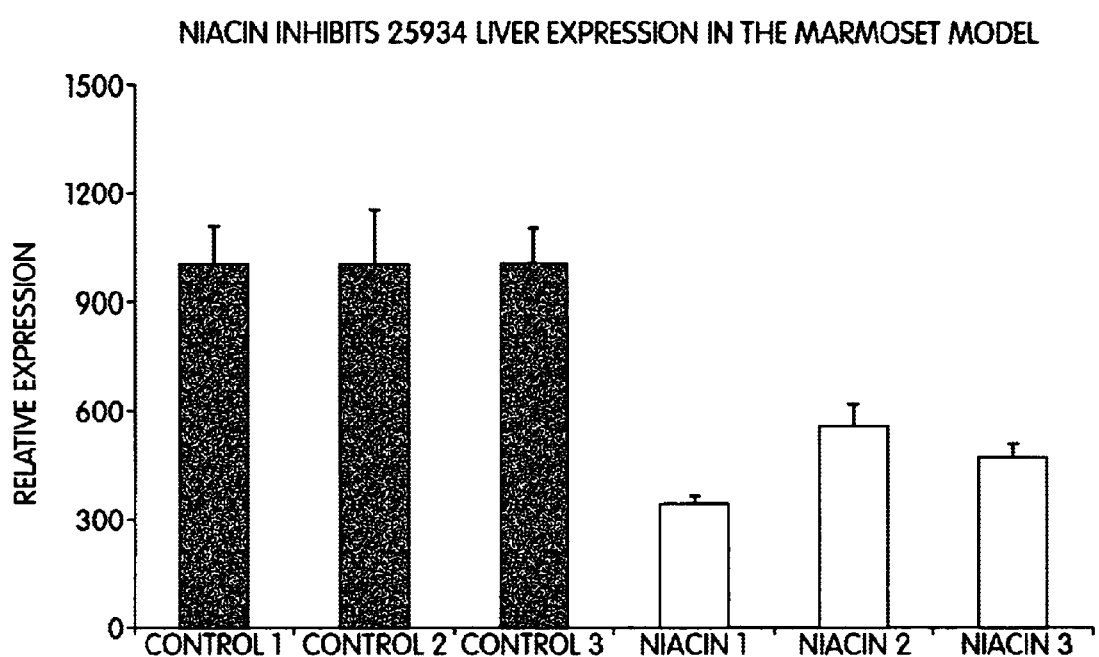
FIG. 7 is a bar graph depicting the inhibition of 25934 mRNA (via TaqMan) expression in the marmoset animal model. Niacin treatment in the marmoset model results in significant repression of 25934 in the liver.

Based on the above-described sequence similarities, the 25934 molecules of the present invention are predicted to have similar biological activities as other desaturase family members, and in particular, stearoyl CoA desaturases (SCD). For example, the 25934 polypeptide or a domain therein, e.g., desaturase domain, may function to catalyze the conversion of a single bond between two carbon atoms (C—C) to a double bond (C=C) in a fatty acid chain. This modification is expected to occur at the n9 position of the fatty acid. Desaturases are predicted to contribute to an unfavorable LDL content state, e.g., by increasing LDL-oleate, which is atherogenic (Rudel, L L. et al. (1997) J. Clin Invest. 1:100(1):74–83) as well as by playing a role in triglyceride metabolism and/or biosynthesis. As shown in FIG. 7, Niacin treatment in the marmoset model results in significant repression of 25934 in the liver. Niacin has been shown to alter the composition of LDL and HDL to a favorable state, to cause a significant reduction in triglycerides, and to increase HDL concentration (Goldberg, A. (2000) Am. J. Cardiol. 85(9):1100–5. Moreover, a mouse deficient for SCD exhibits significant reduction in triglycerides (Miyazaki, M. et al. (2000) J. Biol. Chem. 275(39):30132–8). Accordingly, the 25934 molecules can act as novel diagnostic targets and therapeutic agents for controlling disorders associated with abnormal or aberrant desaturase activity and/or triglyceride levels. In particular, it is predicted that targeting the inhibition of 25934 nucleic acids and polypeptides will results in the favorable modification, and possible reduction, of LDL content and/or reduction of triglycerides. Thus, the 25934 molecules can act as novel targets for treating and/or diagnosing fatty acid metabolic disorders (e.g., desaturation of fatty acids) such as obesity and/or diabetes and more generally, cardiovascular disorders.

Preferred examples of cardiovascular disorders or diseases include e.g., atherosclerosis, thrombosis, heart failure, ischemic heart disease, angina pectoris, myocardial infarction, sudden cardiac death, hypertensive heart disease; non-coronary vessel disease, such as arteriolosclerosis, small vessel disease, nephropathy, hypertriglyceridemia, hypercholesterolemia, hyperlipidemia, asthma, hypertension, emphysema and chronic pulmonary disease; or a cardiovascular condition associated with interventional procedures ("procedural vascular trauma"), such as restenosis following angioplasty, placement of a shunt, stet, stent, synthetic or natural excision grafts, indwelling catheter, valve or other implantable devices.

The term "cardiovascular disorders" or "disease" includes heart disorders, as well as disorders of the blood vessels of the circulation system caused by, e.g., abnormally high concentrations of lipids in the blood vessels.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts--late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As used herein, the term "atherosclerosis" is intended to have its clinical meaning. This term refers to a cardiovascular condition occurring as a result of narrowing down of the arterial walls. The narrowing is due to the formation of plaques (raised patches) or streaks in the inner lining of the arteries. These plaques consist of foam cells of low-density lipoproteins, oxidized-LDL, decaying muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increase with age, causing loss of the smooth lining of the blood vessels and encouraging the formation of thrombi (blood clots). Sometimes fragments of thrombi break off and form emboli, which travel through the bloodstream and block smaller vessels. The blood supply is restricted to the heart, eventually forming a blood clot leading to death. The major causes of atherosclerosis are hypercholesterolemia (and low HDL), hypoalphoproteinemia, and hyperlipidemia marked by high circulating cholesterol and high lipids like LDL-cholesterol and triglycerides in the blood. These lipids are deposited in the arterial walls, obstructing the blood flow and forming atherosclerotic plaques leading to death.

As used herein the term "hypercholesterolemia" is a condition with elevated levels of circulating total cholesterol, LDL-cholesterol and VLDL-cholesterol as per the guidelines of the Expert Panel Report of the National Cholesterol Educational Program (NCEP) of Detection, Evaluation of Treatment of high cholesterol in adults (see, Arch. Int. Med. (1988) 148, 36–39).

As used herein the term "hyperlipidemia" or "hyperlipemia" is a condition where the blood lipid parameters are elevated in the blood. This condition manifests an abnormally high concentration of fats. The lipid fractions in the circulating blood are, total cholesterol, low density lipoproteins, very low density lipoproteins and triglycerides.

As used herein the term "lipoprotein" such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

As used herein, the term "triglyceride" means a lipid or neutral fat consisting of glycerol combined with three fatty acid molecules.

As used herein the term "xanthomatosis" is a disease evidenced by a yellowish swelling or plaques in the skin resulting from deposits of fat. The presence of xanthomas are usually accompanied by raised blood cholesterol levels.

As used herein the term "apolipoprotein B" or "apoprotein B" or "Apo B" refers to the protein component of the LDL cholesterol transport proteins. Cholesterol synthesized de novo is transported from the liver and intestine to peripheral tissues in the form of lipoproteins. Most of the apolipoprotein B is secreted into the circulatory system as VLDL.

As used herein the term "apolipoprotein A" or "apoprotein A" or "Apo A" refers to the protein component of the HDL cholesterol transport proteins.

"Procedural vascular trauma" includes the effects of surgical/medical-mechanical interventions into mammalian vasculature, but does not include vascular trauma due to the organic vascular pathologies listed hereinabove, or to unintended traumas, such as due to an accident. Thus, procedural vascular traumas within the scope of the present treatment method include (1) organ grafting or transplantation, such as transplantation and grafting of heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, or indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arteriovenous communications; and (6) placement of an intravascular stent, which may be metallic, plastic or a biodegradable polymer. See U.S. patent application Ser. No. 08/389, 712, filed Feb. 15, 1995, which is incorporated by reference herein. For a general discussion of implantable devices and biomaterials from which they can be formed, see H. Kambic et al., "Biomaterials in Artificial Organs", Chem. Eng. News, 30 (Apr. 14, 1986), the disclosure of which is incorporated by reference herein.

Small vessel disease includes, but is not limited to, vascular insufficiency in the limbs, peripheral neuropathy and retinopathy, e.g., diabetic retinopathy.

In some embodiments, the therapeutic and prophylactic uses of the compositions of the invention, further include the administration of cholesterol lowering agents as a combination drug therapies. The term "combination therapy" as used herein refers to the administration to a subject (concurrently or sequentially) of two or more cholesterol lowering agents. Current combination therapy therapies using combinations of niacin and statins are being used with positive results to treat hyperlipidemia (Guyton, J R. (1999) Curr Cardiol Rep. 1(3):244–250; Otto, C. et al. (1999) Internist (Berl) 40(12):1338–45). Other useful drug combinations include those derived by addition of fish oil, bile acid binding resins, or stanol esters, as well as nonstatin combinations susn as niacin-resin or fibrate-niacin (Guyton, J R. (1999) supra). For examples of dosages and administration schedules of the cholesterol lowering agents, the teachings of Guyton, J R. (1999) supra, Otto, C. et al. (1999) supra, Guyton, J R et al. (1998) Am J Cardiol 82(12A):82U–86U; Guyton, J R et al. (1998) Am J Cardiol. 82(6):737–43; Vega, G L et al. (1998) Am J. Cardiol. 81(4A):36B–42B; Schectman, G. (1996) Ann Intern Med. 125(12):990–1000; Nakamura, H. et al. (1993) Nippon Rinsho 51(8):2101–7; Goldberg, A. et al. (2000) Am J Cardiol 85(9):1100–5; Morgan, J M et al. (1996) J Cardiovasc. Pharmac. Ther. 1(3):195–202; Stein, E A et al. (1996) J Cardiovasc Pharmacol Ther 1(2):107–116; and Goldberg, A C (1998) Am J Cardiol 82(12A):35U–41U, are expressly incorporated by reference.

As used herein, "cholesterol lowering agents" include agents which are useful for lowering serum cholesterol such as for example bile acid sequestering resins (e.g. colestipol hydrochloride or cholestyramine), fish oil, stanol esters, an ApoAII-lowering agent, a VLDL lowering agent, an ApoAI-stimulating agent, fibric acid derivatives (e.g. clofibrate, fenofibrate, or gemfibrozil), thiazolidenediones (e.g. troglitazone), or HMG-CoA reductase inhibitors (e.g. statins, such as fluvastatin sodium, lovastatin, pravastatin sodium, or simvastatin), as well as nicotinic acid, niacin, or probucol.

"VLDL-lowering agent" includes an agent which decreases the hepatic synthesis of triglyceride-rich lipoproteins or increases the catabolism of triglyceride-rich lipoproteins, e.g., fibrates such as gemfibrozil, or the statins, increases the expression of the apoE-mediated clearance pathway, or improves insulin sensitivity in diabetics, e.g., the thiazolidene diones.

The 25934 molecules can also be used to treat, diagnose or prevent lipid disorders. Examples of lipid disorders include those disorders which affect fatty acid metabolism. Fatty acids are synthesized from acetyl-CoA, which is derived from carbohydrate, protein and other non-lipid sources, and the pathway produces saturated fatty acids, predominantly palmitic acid (10:0). In mammals, the fatty acids may be elongated and desaturated. Desaturation is catalyzed by desaturases which function by inserting one or more double bonds at positions up to 9 carbons from the carboxyl end of a fatty acid molecule.

The degree of fatty acid desaturation in cell membrane lipids determines membrane fluidity. The activity of the desaturase enzyme is critical for maintaining the ratio of saturated and unsaturated fatty acids in cell membranes. Alterations in this ratio can, e.g., alter the physical properties of membranes. Moreover, alterations in the ratio of fatty acids have been implicated in a range of diseases including diabetes, obesity, hypertension, cancer, developmental disorders, immune disorders and neurological and the above-described heart diseases. For example, tumor tissue and virus-transformed cells have a higher content of unsaturated fatty acids, especially oleic acid. Such shifts increase the metabolic rates of many lipid-dependent enzymes and are associated with a higher capacity for cell division.

Figure 4:
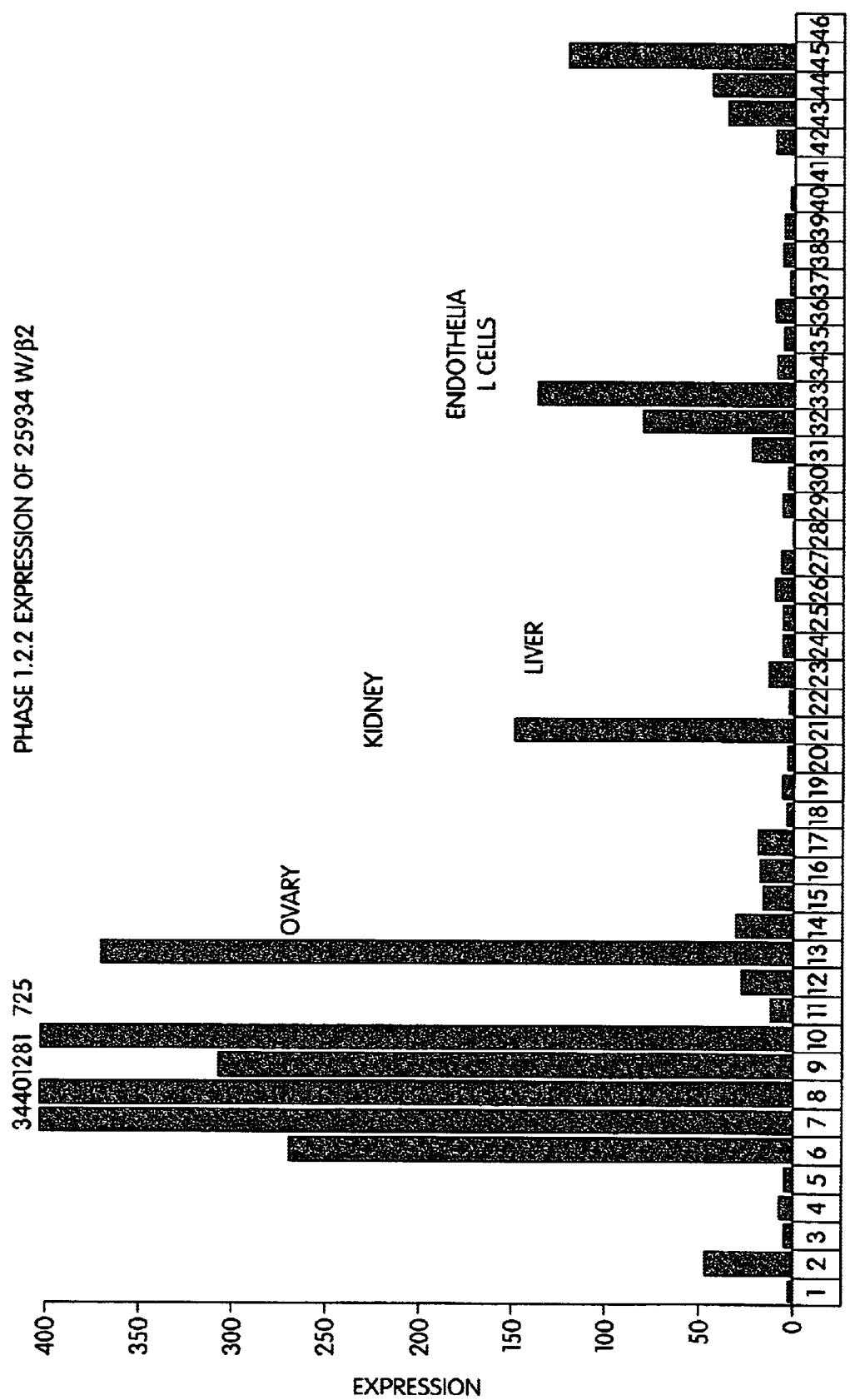
FIG. 4 is a bar graph depicting relative 25934 mRNA expression as determined by TaqMan assays on mRNA derived from the human fetal heart, spinal cord, brain (cortex, hypothalamus, glial cells), ovary, kidney, liver, endothelial cells and smooth muscle cells (SMC). Numbers on the X axis of the bar graph correspond to the following tissues: 1) Aorta Normal; 2) Fetal Heart; 3) Heart Normal; 4) Heart CHF; 5) Vein Normal; 6) Spinal Cord; 7) Brain Cortex; 8) Brain Hypothalamus; 9) Glial Cell Astroc; 10) Brain Glioblast; 11) Breast Normal; 12) Breast Tumor; 13) Ovary Normal; 14) Ovary Tumor; 15) Pancreas; 16) Prostate; 17) Prostate; 18) Colon Normal; 19) Colon Tumor; 20) Colon IBD; 21) Kidney Normal; 22) Liver Normal; 23) Liver Fibrosis; 24) Fetal Liver No; 25) Lung Normal; 26) Lung Tumor; 27) Lung COPD; 28) Spleen Normal; 29) Tonsil Normal; 30) Lymph Node; 31) Thymus Normal; 32) Epithelial Cells; 33) Endothelial Cells; 34) Skeletal Muscle; 35) Fibroblast; 36) Skin Normal; 37) Adipose Normal; 38) Osteoblast; 39) Osteoblast; 40) Osteoblast Diff; 41) Osteoclasts; 42) Aortic SMC; 43) Aortic SMC; 44)Shear HUVEC; 45) Static HUVEC; and 46) BM MNC. The highest 25934 mRNA expression, i.e., greater than 200 relative units, was observed in spinal cord, brain and ovary. High level mRNA expression, i.e., greater than 100 relative units was observed in the kidney, endothelial cells and human umbilical vein endothelial cells (HUVEC). Expression in liver was positive albeit low.
Figure 5:
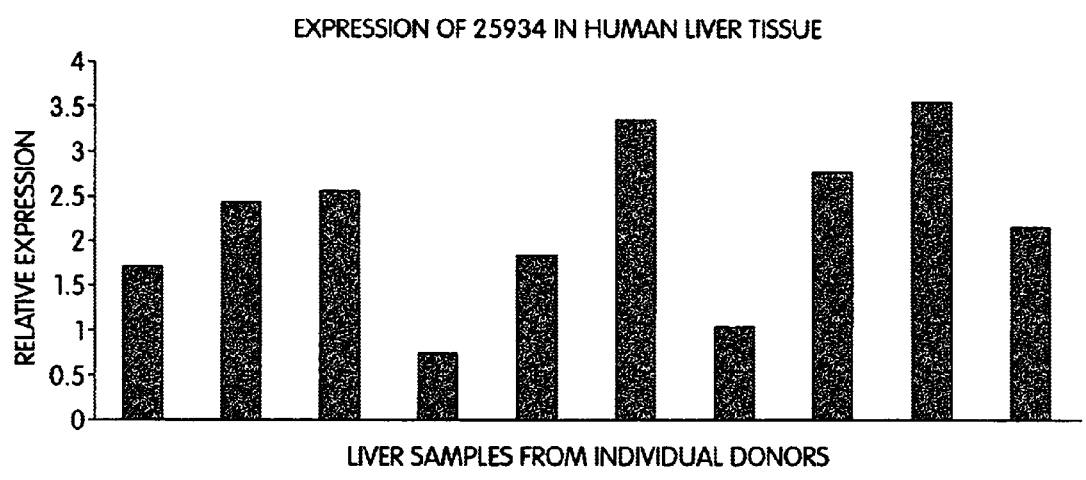
FIG. 5 is a bar graph depicting relative 25934 mRNA expression as determined by TaqMan assays on mRNA derived from an array of human liver tissues from individual donors.
Figure 6:
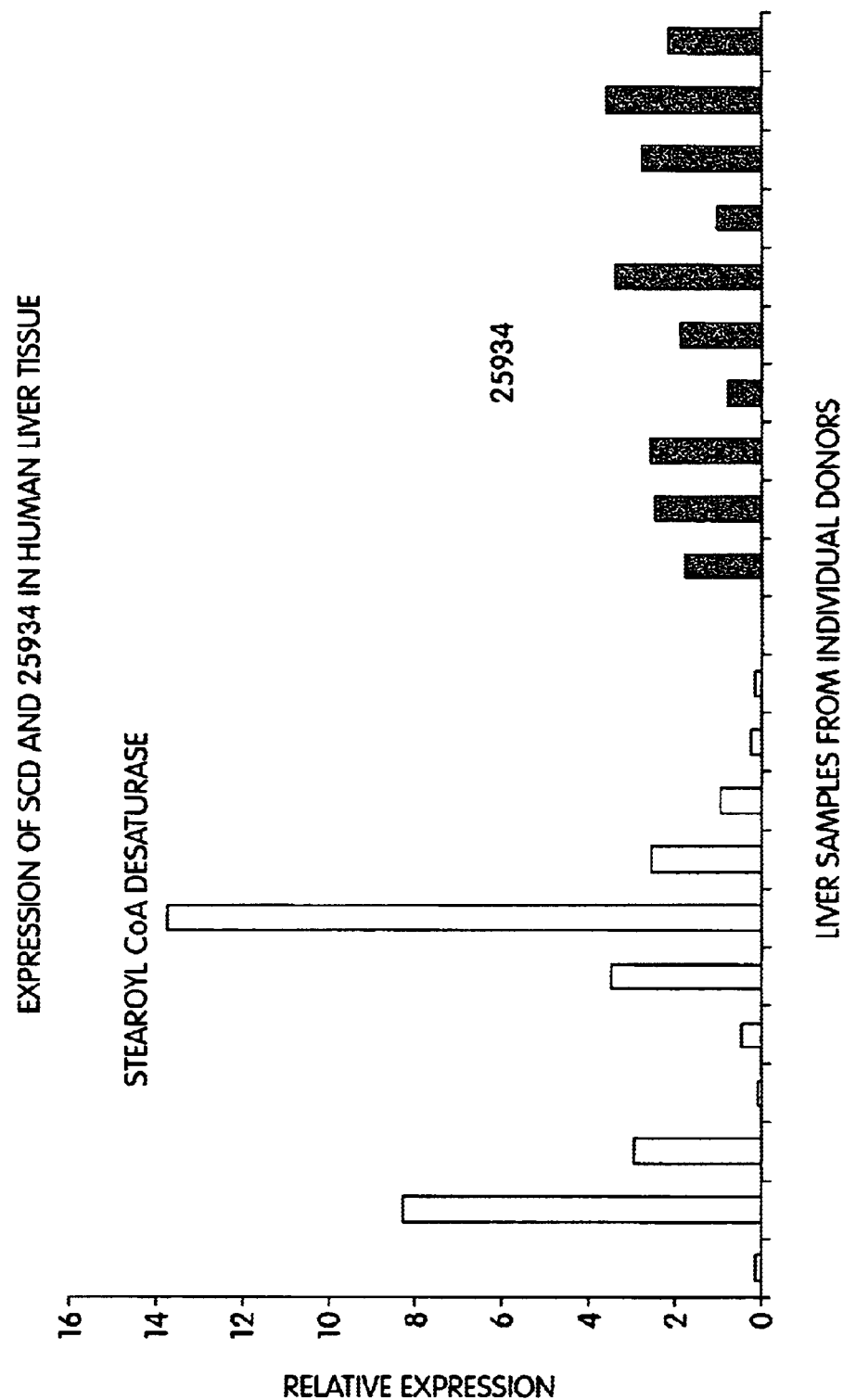
FIG. 6 depicts a comparison of the expression of 25934 mRNA and stearoyl CoA desaturase (SCD) mRNA in a human liver samples from individual donors. Expression of 25934 mRNA in human liver is equivalent to the relative expression of the SCD gene.

As the 25934 mRNA is found in the brain, ovary, kidney and liver, the molecules of the invention can be used to develop novel agents or compounds to treat, prevent and/or diagnose disorders involving aberrant activities of those cells (FIGS. 4–6). For example, the molecules of the invention can be used to treat, present and/or diagnose neurological, reproductive (ovarian), renal and hepatic disorders, as described below.

The 25934 protein, fragments thereof, and derivatives and other variants of the sequence in SEQ ID NO:2 thereof are collectively referred to as "polypeptides or proteins of the invention" or "25934 polypeptides or proteins". Nucleic acid molecules encoding such polypeptides or proteins are collectively referred to as "nucleic acids of the invention" or "25934 nucleic acids." 25934 molecules refer to 25934 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within the hybridization limits of the claim) are 0.5M Sodium Phosphate, 7% SDS at 65° C., followed by one or more washes at 0.2×SSC, 1% SDS at 65°

C. Preferably, an isolated nucleic acid molecule of the invention that hybridizes under stringent conditions to the sequence of SEQ ID NO:1 or 3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 25934 protein, preferably a mammalian 25934 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 25934 protein having less than about 30%, 20%, 10% and more preferably 5% (by dry weight), of non-25934 protein (also referred to herein as a "contaminating protein"), or of chemical precursors or non-25934 chemicals. When the 25934 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 25934 (e.g., the sequence of SEQ ID NO:1 or 3, or the nucleotide sequence of the DNA insert of the plasmid deposited with ATCC as Accession Number 2167) without abolishing or more preferably, without substantially altering a biological activity, whereas an "essential" amino acid residue results in such a change. For example, amino acid residues that are conserved among the polypeptides of the present invention, e.g., those present in the desaturase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 25934 protein is preferably replaced with another amino acid residue from the same side chain family. Alternatively, in another embodiment, mutations can be introduced randomly along all or part of a 25934 coding sequence, such as by saturation mutagenesis, and the resultant mutants can be screened for 25934 biological activity to identify mutants that retain activity. Following mutagenesis of SEQ ID NO:1 or 3, or the nucleotide sequence of the DNA insert of the plasmid deposited with ATCC as Accession Number 2167, the encoded protein can be expressed recombinantly and the activity of the protein can be determined.

As used herein, a "biologically active portion" of a 25934 protein includes a fragment of a 25934 protein which participates in an interaction between a 25934 molecule and a non-25934 molecule. Biologically active portions of a 25934 protein include peptides comprising amino acid sequences sufficiently homologous to or derived from the amino acid sequence of the 25934 protein, e.g., the amino acid sequence shown in SEQ ID NO:2, which include less amino acids than the full length 25934 proteins, and exhibit at least one activity of a 25934 protein. Typically, biologically active portions comprise a domain or motif with at least one activity of the 25934 protein, e.g., 1) catalyzing the formation of a double bond at positions up to 9 carbons from the carboxyl end of a molecule; (2) modulating the synthesis of monounsaturated fatty acids; (3) modulating the desaturation of a fatty acid, e.g., a polyunsaturated fatty acids; (4) modulating cellular lipid composition; (5) modulating the energy state of adipocytes; (6) modulating membrane fluidity; (7) modulating lipid storage; (8) modulating cell proliferation and/or differentiation; (9) modulating lipoprotein (e.g., LDL) composition and/or concentration; (10) regulating triglyceride synthesis; (11) altering the HDL/LDL ration; or (12) modulating fatty acid metabolism. A biologically active portion of a 25934 protein can be a polypeptide which is, for example, 50, 100, 200 or more amino acids in length. Biologically active portions of a 25934 protein can be used as targets for developing agents which modulate a 25934 mediated activity, e.g., a 25934 mediated activity as described above.

Particular 25934 polypeptides of the present invention have an amino acid sequence sufficiently identical to the amino acid sequence of SEQ ID NO:2. The term "sufficiently identical" or "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60–65% identity, likely 66–70%, 75% identity, more likely 85%, 90%. 91%, 92%, 93%, 94%, 95%, 96%, 97%, 98% or 99% identity are defined herein as sufficiently or substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 25934 amino acid sequence of SEQ ID NO:2 having 20 amino acid residues, at least 50, preferably at least 100, more preferably at least 200, even more preferably at least 300, and even more preferably at least 320, or 330 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if the molecule is within the sequence identity limits of a claim) is using Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 25934 nucleic acid molecules of the invention. BLAST protein searches can be performed with the XBLAST program, score=50, wordlength=3 to obtain amino acid sequences homologous to 25934 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 25934 polypeptide described herein, e.g., a full length 25934 protein or a fragment thereof, e.g., a biologically active portion of 25934 protein. Also included is a nucleic acid fragment suitable for use as a hybridization probe, which can be used, e.g., to a identify nucleic acid molecule encoding a polypeptide of the invention, 25934 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or the nucleotide sequence of the DNA insert of the plasmid deposited with ATCC as Accession Number 2167, or a portion of any of these nucleotide sequences. In one embodiment, the nucleic acid molecule includes sequences encoding the human 25934 protein (i.e., "the coding region", from nucleotides 403–1392 of SEQ ID NO:1), as well as 5' untranslated sequence (nucleotides 1–402 of SEQ ID NO:1) and a 3' untranslated sequence (nucleotides 1393–1512). Alternatively, the nucleic acid molecule can include only the coding region of SEQ ID NO:1 (e.g., nucleotides 1–990, corresponding to SEQ ID NO:3) and, e.g., no flanking sequences which normally accompany the subject sequence.

In another embodiment, an isolated nucleic acid molecule of the invention includes a nucleic acid molecule which is a complement of the nucleotide sequence shown in SEQ ID NO:1 or 3, or the nucleotide sequence of the DNA insert of the plasmid deposited with ATCC as Accession Number 2167, or a portion of any of these nucleotide sequences. In other embodiments, the nucleic acid molecule of the invention is sufficiently complementary to the nucleotide sequence shown in SEQ ID NO:1 or 3, or the nucleotide sequence of the DNA insert of the plasmid deposited with ATCC as Accession Number 2167 such that it can hybridize to the nucleotide sequence shown in SEQ ID NO:1 or 3, or the nucleotide sequence of the DNA insert of the plasmid deposited with ATCC as Accession Number 2167, thereby forming a stable duplex.

In one embodiment, an isolated nucleic acid molecule of the present invention includes a nucleotide sequence which is at least about: 60%, 65%, 66–69%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or 3, or the entire length of the nucleotide sequence of the DNA insert of the plasmid deposited with ATCC as Accession Number 2167, or a portion, preferably of the same length, of any of these nucleotide sequences.

25934 Nucleic Acid Fragments

A nucleic acid molecule of the invention can include only a portion of the nucleic acid sequence of SEQ ID NO:1 or 3, or the nucleotide sequence of the DNA insert of the plasmid deposited with ATCC as Accession Number 2167. For example, such a nucleic acid molecule can include a fragment which can be used as a probe or primer or a fragment encoding a portion of a 25934 protein, e.g., an immunogenic or biologically active portion of a 25934 protein. A fragment can comprise nucleotides 555 to 1287 of SEQ ID NO:1, which encodes a desaturase domain of human 25934. The nucleotide sequence determined from the cloning of the 25934 gene allows for the generation of probes and primers designed for use in identifying and/or cloning other 25934 family members, or fragments thereof, as well as 25934 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50, 90, 120, 150, 200, or 244 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the fragment can include a desaturase domain and a protein kinase C phosphorylation site.

25934 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or 3, or the nucleotide sequence of the DNA insert of the plasmid deposited with ATCC as Accession Number 2167, or of a naturally occurring allelic variant or mutant of SEQ ID NO:1 or 3, or the nucleotide sequence of the DNA insert of the plasmid deposited with ATCC as Accession Number 2167.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a desaturase domain: amino acids 51 to 295 of SEQ ID NO:2.

In another embodiment a set of primers is provided, e.g., primers suitable for use in a PCR, which can be used to amplify a selected region of a 25934 sequence. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying a domain or region described herein, e.g., a desaturase domain which occurs at amino acids 51 to 295 of SEQ ID NO:2, are provided.

A nucleic acid fragment can encode an epitope bearing region of a polypeptide described herein.

A nucleic acid fragment encoding a "biologically active portion of a 25934 polypeptide" can be prepared by isolating a portion of the nucleotide sequence of SEQ ID NO:1 or 3, or the nucleotide sequence of the DNA insert of the plasmid deposited with ATCC as Accession Number 2167, which encodes a polypeptide having a 25934 biological activity (e.g., the biological activities of the 25934 proteins are described herein), expressing the encoded portion of the 25934 protein (e.g., by recombinant expression in vitro) and assessing the activity of the encoded portion of the 25934 protein. For example, a nucleic acid fragment encoding a biologically active portion of 25934 includes a desaturase domain, e.g., amino acid residues 51 to 295 of SEQ ID NO:2. A nucleic acid fragment encoding a biologically active portion of a 25934 polypeptide, may comprise a nucleotide sequence which is greater 350 or more nucleotides in length (e.g., greater than about 400 nucleotides in length).

In preferred embodiment, the fragment is at least 604, 650, 700, 750, 800, 850, 900, 950, 1000, 1100, 1200, 1300, 1400, 1500 nucleotides in length, or more nucleotides in length and hybridizes under stringent hybridization conditions to a nucleic acid molecule of SEQ ID NO:1, or SEQ ID NO:3, or the nucleotide sequence of the DNA insert of the plasmid deposited with ATCC as Accession Number 2167.

In a preferred embodiment, a nucleic acid fragment includes a nucleotide sequence comprising nucleotides SEQ ID NO:1 or SEQ ID NO:3, or a portion thereof, wherein each portion is about 604 or longer nucleotides and hybridizes under stringent hybridization conditions to a nucleic acid molecule of SEQ ID NO:1, or SEQ ID NO:3, or the nucleotide sequence of the DNA insert of the plasmid deposited with ATCC as Accession Number 2167. In other embodiments, a nucleic acid fragment includes a nucleotide sequence of about 466 or more nucleotides in length which comprises nucleotides 1–709 of SEQ ID NO:1; or about 604 or more nucleotides in length which comprises nucleotides 710–1669 of SEQ ID NO:1.

In a preferred embodiment, a nucleic acid fragment has a nucleotide sequence other than (e.g., differs by at least one, two, three, five, ten or more nucleotides from) the nucleotide sequence of sequence of AI 401562, AI 942480, AW 131469, BE 515130, W 28157, BE 244746, AI 815730, or AI 816228.

25934 Nucleic Acid Variants

The invention further encompasses nucleic acid molecules that differ from the nucleotide sequence shown in SEQ ID NO:1 or 3, or the nucleotide sequence of the DNA insert of the plasmid deposited with ATCC as Accession Number 2167. Such differences can be due to degeneracy of the genetic code (and result in a nucleic acid which encodes the same 25934 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. E.g., the nucleic acid can be one in which at least one colon, at preferably at least 10%, or 20% of the codons has been altered such that the sequence is optimized for expression in e. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, or the sequence in ATCC Accession Number 2167, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Nucleic acid molecules corresponding to orthologs, homologs, and allelic variants of the 25934 cDNAs of the invention can further be isolated by mapping to the same chromosome or locus as the 25934 gene.

Preferred variants include those that are correlated with (1) catalyzing the formation of a double bond, preferably, at positions up to 9 carbons from the carboxyl end of a molecule, e.g., a fatty acid, such as a polyunsaturated fatty acid; (2) modulating the synthesis of monounsaturated fatty acids, e.g., modulating the synthesis of a fatty acid synthesized in an animal, e.g., oleic acid, palmitoyl- and stearoyl-CoA; (3) modulating the desaturation of a fatty acid, e.g., a polyunsaturated fatty acids; (4) modulating cellular lipid composition, e.g., modulating the ratio of saturated and unsaturated fatty acids; (5) modulating the energy state of adipocytes; (6) modulating membrane fluidity; (7) modulating lipid storage; (8) modulating proliferation and/or differentiation; (9) modulating lipoprotein (e.g., LDL) composition and/or concentration; (10) regulating triglyceride synthesis; (11) altering the HDL/LDL ration; (12) modulating fatty acid metabolism; or (13) modulating the development of atherosclerotic lesions in disease models.

Allelic variants of 25934, e.g., human 25934, include both functional and non-functional proteins. Functional allelic variants are naturally occurring amino acid sequence variants of the 25934 protein within a population that maintain the ability to (1) catalyzing the formation of a double bond, preferably, at positions up to 9 carbons from the carboxyl end of a molecule, e.g., a fatty acid, such as a polyunsaturated fatty acid; (2) modulating the synthesis of monounsaturated fatty acids, e.g., modulating the synthesis of a fatty acid synthesized in an animal, e.g., oleic acid, palmitoyl- and stearoyl-CoA; (3) modulating the desaturation of a fatty acid, e.g., a polyunsaturated fatty acids; (4) modulating cellular lipid composition, e.g., modulating the ratio of saturated and unsaturated fatty acids; (5) modulating the energy state of adipocytes; (6) modulating membrane fluidity; (7) modulating lipid storage; (8) modulating proliferation and/or differentiation; (9) modulating lipoprotein (e.g., LDL) composition and/or concentration; (10) regulating triglyceride synthesis; (11) altering the HDL/LDL ration; or (12) modulating fatty acid metabolism. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 25934, e.g., human 25934, protein within a population that do not have the ability to modulate a 25934-mediated activity as described herein. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 25934 family members and, thus, which have a nucleotide sequence which differs from the 25934 sequences of SEQ ID NO:1 or 3, or the nucleotide sequence of the DNA insert of the plasmid deposited with ATCC as Accession Number 2167 are intended to be within the scope of the invention.

Antisense Nucleic Acid Molecules, Ribozymes and Modified 25934 Nucleic Acid Molecules In another aspect, the invention features, an isolated nucleic acid molecule which is antisense to 25934. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 25934 coding strand, or to only a portion thereof (e.g., the coding region of human 25934 corresponding to SEQ ID NO:3). In another embodiment, the antisense nucleic acid molecule is antisense to a "noncoding region" of the coding strand of a nucleotide sequence encoding 25934 (e.g., the 5' and 3' untranslated regions).

An antisense nucleic acid can be designed such that it is complementary to the entire coding region of 25934 mRNA, but more preferably is an oligonucleotide which is antisense to only a portion of the coding or noncoding region of 25934 mRNA. For example, the antisense oligonucleotide can be complementary to the region surrounding the translation start site of 25934 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 25934 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 25934-encoding nucleic acid can include one or more sequences complementary to the the nucleotide sequence of a 25934 cDNA disclosed herein (i.e., SEQ ID NO:1 or 3), and a sequence having known catalytic sequence responsible for mRNA cleavage (see U.S. Pat. No. 5,093,246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 25934-encoding mRNA. See, e.g., Cech et al. U.S. Pat. No. 4,987,071; and Cech et al. U.S. Pat. No. 5,116,742. Alternatively, 25934 mRNA can be used to select a catalytic RNA having a specific ribonuclease activity from a pool of RNA molecules. See, e.g., Bartel, D. and Szostak, J. W. (1993) *Science* 261:1411–1418.

25934 gene expression can be inhibited by targeting nucleotide sequences complementary to the regulatory region of the 25934 (e.g., the 25934 promoter and/or enhancers) to form triple helical structures that prevent transcription of the 25934 gene in target cells. See generally, Helene, C. (1991) *Anticancer Drug Des.* 6(6):569–84; Helene, C. et al. (1992) *Ann. N.Y Acad. Sci.* 660:27–36; and Maher, L. J. (1992) *Bioassays* 14(12):807–15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 25934 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 25934 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 25934 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 25934 nucleic acid of the invention, two complementary regions one having a fluorophore and one a quencher such that the molecular beacon is useful for quantitating the presence of the 25934 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 25934 Polypeptides

In another aspect, the invention features, an isolated 25934 protein, or fragment, e.g., a biologically active portion, for use as immunogens or antigens to raise or test (or more generally to bind) anti-25934 antibodies. 25934 protein can be isolated from cells or tissue sources using standard protein purification techniques. 25934 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, a 25934 polypeptide has one or more of the following characteristics:

(i) it has the ability to promote the formation of a double bond at positions up to 9 carbons from the carboxyl end of a molecule;

(ii) it has a molecular weight (e.g., a deduced molecular weight), amino acid composition or other physical characteristic of the protein of SEQ ID NO:2;

(iii) it has an overall sequence similarity of at least 65–69%, preferably at least 70, 80, 90, or 95%, with a polypeptide of SEQ ID NO:2;

(iv) it has a desaturase domain which is preferably about 70%, 80%, 90% or 95% with amino acid residues 51–295 of SEQ ID NO:2;

(v) it has the fatty acid desaturase signature (ProSite PS00476) at about residues 268 to 282 of SEQ ID NO:2;

(vi) it has eight conserved histidines which can coordinate the iron active site at about residues 94, 99, 131, 134, 135, 272, 275, and 276 of SEQ ID NO:2; or (vii) it has at least 70%, preferably 80%, and most preferably 90% of the cysteines found amino acid sequence of the native protein.

In a preferred embodiment the 25934 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. The differences are, preferably, differences or changes at a non-essential residue or a conservative substitution. In a preferred embodiment the differences are not in the desaturase domain. In another preferred embodiment, one or more differences are in the desaturase domain.

Other embodiments include a protein that contain one or more changes in amino acid sequence, e.g., a change in an amino acid residue which is not essential for activity. Such 25934 proteins differ in amino acid sequence from SEQ ID NO:2, yet retain biological activity.

In one embodiment, the protein includes an amino acid sequence at least about 60%, 65%, 66–69%, 70%, 75%, 80%, 85%, 90%, 95%, 98% or more homologous to SEQ ID NO:2.

A 25934 protein or fragment is provided which varies from the sequence of SEQ ID NO:2 in non-active site residues by at least one but by less than 15, 10 or 5 amino acid residues in the protein or fragment, but which does not differ from SEQ ID NO:2 in regions having desaturase activity. In some embodiments, the difference is at a non-essential residue or is a conservative substitution, while in others the difference is at an essential residue or is a non conservative substitution.

In one embodiment, a biologically active portion of a 25934 protein includes desaturase domain. Moreover, other biologically active portions, in which other regions of the protein are deleted, can be prepared by recombinant techniques and evaluated for one or more of the functional activities of a native 25934 protein.

In a preferred embodiment, the 25934 protein has an amino acid sequence shown in SEQ ID NO:2. In other embodiments, the 25934 protein is substantially identical to SEQ ID NO:2. In yet another embodiment, the 25934 protein is substantially identical to SEQ ID NO:2 and retains the functional activity of the protein of SEQ ID NO:2, as described in detail in the subsections above.

25934 Chimeric or Fusion Proteins

In another aspect, the invention provides 25934 chimeric or fusion proteins. As used herein, a 25934 "chimeric protein" or "fusion protein" includes a 25934 polypeptide linked to a non-25934 polypeptide. A "non-25934 polypeptide" refers to a polypeptide having an amino acid sequence corresponding to a protein which is not substantially homologous to the 25934 protein, e.g., a protein which is different from the 25934 protein and which is derived from the same or a different organism. The 25934 polypeptide of the fusion protein can correspond to all or a portion e.g., a fragment described herein of a 25934 amino acid sequence. In a preferred embodiment, a 25934 fusion protein includes at least one (or two) biologically active portion of a 25934 protein. The non-25934 polypeptide can be fused to the N-terminus or C-terminus of the 25934 polypeptide.

The fusion protein can include a moiety which has a high affinity for a ligand. For example, the fusion protein can be a GST-25934 fusion protein in which the 25934 sequences are fused to the C-terminus of the GST sequences. Such fusion proteins can facilitate the purification of recombinant 25934. Alternatively, the fusion protein can be a 25934 protein containing a heterologous signal sequence at its N-terminus. In certain host cells (e.g., mammalian host cells), expression and/or secretion of 25934 can be increased through use of a heterologous signal sequence.

Fusion proteins can include all or a part of a serum protein, e.g., an IgG constant region, or human serum albumin.

The 25934 fusion proteins of the invention can be incorporated into pharmaceutical compositions and administered to a subject in vivo. The 25934 fusion proteins can be used to affect the bioavailability of a 25934 substrate. 25934 fusion proteins may be useful therapeutically for the treatment of disorders caused by, for example, (i) aberrant modification or mutation of a gene encoding a 25934 protein; (ii) mis-regulation of the 25934 gene; and (iii) aberrant post-translational modification of a 25934 protein.

Moreover, the 25934-fusion proteins of the invention can be used as immunogens to produce anti-25934 antibodies in a subject, to purify 25934 ligands and in screening assays to identify molecules which inhibit the interaction of 25934 with a 25934 substrate.

Expression vectors are commercially available that already encode a fusion moiety (e.g., a GST polypeptide). A 25934-encoding nucleic acid can be cloned into such an expression vector such that the fusion moiety is linked in-frame to the 25934 protein.

Variants of 25934 Proteins

In another aspect, the invention also features a variant of a 25934 polypeptide, e.g., which functions as an agonist (mimetics) or as an antagonist. Variants of the 25934 proteins can be generated by mutagenesis, e.g., discrete point mutation, the insertionor deletion of sequences or the truncation of a 25934 protein. An agonist of the 25934 proteins can retain substantially the same, or a subset, of the biological activities of the naturally occurring form of a 25934 protein. An antagonist of a 25934 protein can inhibit one or more of the activities of the naturally occurring form of the 25934 protein by, for example, competitively modulating a 25934-mediated activity of a 25934 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 25934 protein.

Variants of a 25934 protein can be identified by screening combinatorial libraries of mutants, e.g., truncation mutants, of a 25934 protein for agonist or antagonist activity.

Libraries of fragments e.g., N terminal, C terminal, or internal fragments, of a 25934 protein coding sequence can be used to generate a variegated population of fragments for screening and subsequent selection of variants of a 25934 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 25934 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 25934 library. For example, a library of expression vectors can be transfected into a cell line, e.g., a cell line, which ordinarily responds to 25934 in a substrate-dependent manner. The transfected cells are then contacted with 25934 and the effect of the expression of the mutant on signaling by the 25934 substrate can be detected, e.g., by measuring the formation of double bonds in the hydrocarbon areas of fatty acids. Plasmid DNA can then be recovered from the cells which score for inhibition, or alternatively, potentiation of signaling by the 25934 substrate, and the individual clones further characterized.

In another aspect, the invention features a method of making a 25934 polypeptide, e.g., a peptide having a non-wild type activity, e.g., an antagonist, agonist, or super agonist of a naturally occurring 25934 polypeptide, e.g., a naturally occurring 25934 polypeptide. The method includes: altering the sequence of a 25934 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 25934 polypeptide a biological activity of a naturally occurring 25934 polypeptide. The method includes: altering the sequence, e.g., by substitution or deletion of one or more residues, of a 25934 polypeptide, e.g., altering the sequence of a non-conserved region, or a domain or residue described herein, and testing the altered polypeptide for the desired activity.

Anti-25934 Antibodies

In another aspect, the invention provides an anti-25934 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

In a preferred embodiment, the antibody fails to bind an Fc receptor, e.g., it is an isotype which does not bind to an Fc receptor, or has been modified, e.g., by deletion or other mutation, such that it does not have a functional Fc receptor binding region.

A full-length 25934 protein or, antigenic peptide fragment of 25934 can be used as an immunogen, or can be used to identify anti-25934 antibodies made with other immunogens, e.g., cells, membrane preparations, and the like. The antigenic peptide of 25934 should include at least 8 amino acid residues of the amino acid sequence shown in SEQ ID NO:2 and encompasses an epitope of 25934. Preferably, the antigenic peptide includes at least 10 amino acid residues, more preferably at least 15 amino acid residues, even more preferably at least 20 amino acid residues, and most preferably at least 30 amino acid residues.

Fragments of 25934 which include residues 30–45, 121–151, or 241–261 can be used to make, e.g., used as immunogens, or used to characterize the specificity of an antibody, antibodies against hydrophilic regions of the 25934 protein. Similarly, a fragment of 25934 which include residues 291–307 can be used to make an antibody against a hydrophobic region of the 25934 protein; a fragment of 25934 which include all or a portion of residues 51–95 can be used to make an antibody against the desaturase domain of the 25934 protein.

Antibodies reactive with, or specific for, any of these regions, or other regions or domains described herein are provided.

Preferred epitopes encompassed by the antigenic peptide are regions of 25934 are located on the surface of the protein, e.g., hydrophilic regions, as well as regions with high antigenicity. For example, an Emini surface probability analysis of the human 25934 protein sequence can be used to indicate the regions that have a particularly high probability of being localized to the surface of the 25934 protein and are thus likely to constitute surface residues useful for targeting antibody production.

In a preferred embodiment the antibody binds an epitope on any domain or region on 25934 proteins described herein.

Chimeric, humanized, but most preferably, completely human antibodies are desirable for applications which include repeated administration, e.g., therapeutic treatment (and some diagnostic applications) of human patients.

The anti-25934 antibody can be a signle chain antibody. A single-chain antibody (scFV) may be engineered (see, for example, Colcher, D., et al. *Ann N Y Acad Sci* Jun. 30, 1999;880:263–80; and Reiter, Y. *Clin Cancer Res* 1996 February;2(2):245–52). The single chain antibody can be dimerized or multimerized to generate multivalent antibodies having specificities for different epitopes of the same target 25934 protein.

An anti-25934 antibody (e.g., monoclonal antibody) can be used to isolate 25934 by standard techniques, such as affinity chromatography or immunoprecipitation. Moreover, an anti-25934 antibody can be used to detect 25934 protein (e.g., in a cellular lysate or cell supernatant) in order to evaluate the abundance and pattern of expression of the protein. Anti-25934 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 25934 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 25934 proteins, mutant forms of 25934 proteins, fusion proteins, and the like).

The recombinant expression vectors of the invention can be designed for expression of 25934 proteins in prokaryotic or eukaryotic cells. For example, polypeptides of the invention can be expressed in *E. coli,* insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 25934 activity assays, (e.g., direct assays or competitive assays described in detail below), or to generate antibodies specific for 25934 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 25934 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter;

Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect the invention provides a host cell which includes a nucleic acid molecule described herein, e.g., a 25934 nucleic acid molecule within a recombinant expression vector or a 25934 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 25934 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 25934 protein. Accordingly, the invention further provides methods for producing a 25934 protein using the host cells of the invention. In one embodiment, the method includes culturing the host cell of the invention (into which a recombinant expression vector encoding a 25934 protein has been introduced) in a suitable medium such that a 25934 protein is produced. In another embodiment, the method further includes isolating a 25934 protein from the medium or the host cell.

In another aspect, the invention features, a cell or purified preparation of cells which include a 25934 transgene, or which otherwise misexpress 25934. The cell preparation can consist of human or non human cells, e.g., rodent cells, e.g., mouse or rat cells, rabbit cells, or pig cells. In preferred embodiments, the cell or cells include a 25934 transgene, e.g., a heterologous form of a 25934, e.g., a gene derived from humans (in the case of a non-human cell). The 25934 transgene can be misexpressed, e.g., overexpressed or underexpressed. In other preferred embodiments, the cell or cells include a gene which misexpress an endogenous 25934, e.g., a gene the expression of which is disrupted, e.g., a knockout. Such cells can serve as a model for studying disorders which are related to mutated or mis-expressed 25934 alleles or for use in drug screening.

In another aspect, the invention features, a human cell, e.g., a hematopoietic stem cell, transformed with nucleic acid which encodes a subject 25934 polypeptide.

Also provided are cells, e.g., human cells, e.g., human hematopoietic or fibroblast cells, in which an endogenous 25934 is under the control of a regulatory sequence that does not normally control the expression of the endogenous 25934 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 25934 gene. For example, an endogenous 25934 gene, e.g., a gene that is "transcriptionally silent", e.g., not normally expressed, or expressed only at very low levels, may be activated by inserting a regulatory element which is capable of promoting the expression of a normally expressed gene product in that cell. Techniques, such as targeted homologous recombination, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 25934 protein and for identifying and/or evaluating modulators of 25934 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangment, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 25934 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 25934 protein to particular cells. A transgenic founder animal can be identified based upon the presence of a 25934 transgene in its genome and/or expression of 25934 mRNA in tissues or cells of the animals. A transgenic founder animal can then be used to breed additional animals carrying the transgene. Moreover, transgenic animals carrying a transgene encoding a 25934 protein can further be bred to other transgenic animals carrying other transgenes.

25934 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 25934 protein (e.g., via a recombinant expression vector in a host cell in gene therapy applications), to detect a 25934 mRNA (e.g., in a biological sample) or a genetic alteration in a 25934 gene, and to modulate 25934 activity, as described further below. The 25934 proteins can be used to treat disorders characterized by insufficient or excessive production of a 25934 substrate or production of 25934 inhibitors. In addition, the 25934 proteins can be used to screen for naturally occurring 25934 substrates, to screen for drugs or compounds which modulate 25934 activity, as well as to treat disorders characterized by insufficient or excessive production of 25934 protein or production of 25934 protein forms which have decreased, aberrant or unwanted activity compared to 25934 wild type protein, e.g., diabetes, obesity, hypertension, cancer, developmental disorders, immune disorders and neurological and heart diseases.

Moreover, the anti-25934 antibodies of the invention can be used to detect and isolate 25934 proteins, regulate the bioavailability of 25934 proteins, and modulate 25934 activity.

A method of evaluating a compound for the ability to interact with, e.g., bind, a subject 25934 polypeptide is provided. The method includes: contacting the compound, e.g., a substrate, with the subject 25934 polypeptide; and evaluating ability of the compound to interact with, e.g., to bind or form a complex with the subject 25934 polypeptide. This method can be performed in vitro, e.g., in a cell free system, or in vivo, e.g., in a two-hybrid interaction trap assay. This method can be used to identify naturally occurring molecules, which interact with subject 25934 polypeptide. It can also be used to find natural or synthetic inhibitors of subject 25934 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 25934 proteins, have a stimulatory or inhibitory effect on, for example, 25934 expression or 25934 activity, or have a stimulatory or inhibitory effect on, for example, the expression or activity of a 25934 substrate. Compounds thus identified can be used to modulate the activity of target gene products (e.g., 25934 genes) in a therapeutic protocol, to elaborate the biological function of the target gene product, or to identify compounds that disrupt normal target gene interactions.

In one embodiment, the invention provides assays for screening candidate or test compounds which are substrates of a 25934 protein or polypeptide or a biologically active portion thereof. In another embodiment, the invention provides assays for screening candidate or test compounds which bind to or modulate the activity of a 25934 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a 25934 protein or biologically active portion thereof is contacted with a test compound, and the ability of the test compound to modulate 25934 activity is determined. Determining the ability of the test compound to modulate 25934 activity can be accomplished by monitoring, for example, determing desaturase activity. The cell, for example, can be of mammalian origin, e.g., a brain, ovarian, kidney, and/or liver cell.

The ability of the test compound to modulate 25934 binding to, or interaction with, a compound, e.g., a 25934 substrate, or to bind to 25934 can also be evaluated. This can be accomplished, for example, by coupling the compound, e.g., the substrate, with a radioisotope or enzymatic label such that binding of the compound, e.g., the substrate, to 25934 can be determined by detecting the labeled compound, e.g., substrate, in a complex. Alternatively, 25934 could be coupled with a radioisotope or enzymatic label to monitor the ability of a test compound to modulate 25934 binding to a 25934 substrate in a complex. For example, compounds (e.g., 25934 substrates) can be labeled with $^{125}I$, $^{35}S$, $^{14}C$, or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 25934 substrate) to interact with 25934 with or without the labeling of any of the interactants can be evaluated. For example, a microphysiometer can be used to detect the interaction of a compound with 25934 without the labeling of either the compound or the 25934. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 25934.

In yet another embodiment, a cell-free assay is provided in which a 25934 protein or biologically active portion thereof is contacted with a test compound and the ability of the test compound to bind to the 25934 protein or biologically active portion thereof is evaluated. Preferred biologically active portions of the 25934 proteins to be used in assays of the present invention include fragments, which participate in interactions with non-25934 molecules, e.g., fragments with high surface probability scores.

Soluble and/or membrane-bound forms of isolated proteins (e.g., 25934 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylaminio]-2-hydroxy-1-propane sulfonate (CHAPSO), or N-dodecyl= N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 25934 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 25934, an anti-25934 antibody or its target molecule to facilitate separation of complexed from uncomplexed forms of one or both of the proteins, as well as to accommodate automation of the assay. Binding of a test compound to a 25934 protein, or interaction of a 25934 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/25934 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 25934 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 25934 binding or activity determined using standard techniques.

Other techniques for immobilizing either a 25934 protein or a target molecule on matrices include using conjugation of biotin and streptavidin. Biotinylated 25934 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 25934 protein or target molecules but which do not interfere with binding of the 25934 protein to its target molecule. Such antibodies can be derivatized to the wells of the plate, and unbound target or 25934 protein trapped in the wells by antibody conjugation. Methods for detecting such complexes, in addition to those described above for the GST-immobilized complexes, include immunodetection of complexes using antibodies reactive with the 25934 protein or target molecule, as well as enzyme-linked assays which rely on detecting an enzymatic activity associated with the 25934 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 August;18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol Recognit* 1998 Winter;11(1–6):141–8; Hage, D. S., and Tweed, S. A. *J Chromatogr B Biomed Sci Appl* Oct. 10, 1997;699(1–2):499–525). Further, fluorescence energy transfer may also be conveniently utilized, as described herein, to detect binding without further purification of the complex from solution.

In a preferred embodiment, the assay includes contacting the 25934 protein or biologically active portion thereof with a known compound which binds 25934 to form an assay mixture, contacting the assay mixture with a test compound, and determining the ability of the test compound to interact with a 25934 protein, wherein determining the ability of the test compound to interact with a 25934 protein includes determining the ability of the test compound to preferentially bind to 25934 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 25934 genes herein identified. In an alternative embodiment, the invention provides methods for determining the ability of the test compound to modulate the activity of a 25934 protein through modulation of the activity of a downstream effector of a 25934 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 25934 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 25934 ("25934-binding proteins" or "25934-bp") and are involved in 25934 activity. Such 25934-bps can be activators or inhibitors of signals by the 25934 proteins or 25934 targets as, for example, downstream elements of a 25934-mediated signaling pathway.

The two-hybrid system is based on the modular nature of most transcription factors, which consist of separable DNA-binding and activation domains. Briefly, the assay utilizes two different DNA constructs. In one construct, the gene that codes for a 25934 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 25934 protein can be the fused to the activator domain.) If the "bait" and the "prey" proteins are able to interact, in vivo, forming a 25934-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 25934 protein.

In another embodiment, modulators of 25934 expression are identified. For example, a cell or cell free mixture is contacted with a candidate compound and the expression of 25934 mRNA or protein evaluated relative to the level of expression of 25934 mRNA or protein in the absence of the candidate compound. When expression of 25934 mRNA or protein is greater in the presence of the candidate compound than in its absence, the candidate compound is identified as a stimulator of 25934 mRNA or protein expression. Alternatively, when expression of 25934 mRNA or protein is less (statistically significantly less) in the presence of the candidate compound than in its absence, the candidate compound is identified as an inhibitor of 25934 mRNA or protein expression. The level of 25934 mRNA or protein expression can be determined by methods described herein for detecting 25934 mRNA or protein.

In another aspect, the invention pertains to a combination of two or more of the assays described herein. For example, a modulating agent can be identified using a cell-based or a cell free assay, and the ability of the agent to modulate the activity of a 25934 protein can be confirmed in vivo, e.g., using an animal model.

This invention further pertains to novel agents identified by the above-described screening assays. Accordingly, it is within the scope of this invention to further use an agent identified as described herein (e.g., a 25934 modulating agent, an antisense 25934 nucleic acid molecule, a 25934-specific antibody, or a 25934-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 25934 with a disease; (ii) identify an individual from a minute biological sample (tissue typing); and (iii) aid in forensic identification of a biological sample. These applications are described in the subsections below.

Chromosome Mapping

The 25934 nucleotide sequences or portions thereof can be used to map the location of the 25934 genes on a chromosome. This process is called chromosome mapping. Chromosome mapping is useful in correlating the 25934 sequences with genes associated with disease.

Briefly, 25934 genes can be mapped to chromosomes by preparing PCR primers (preferably 15–25 bp in length) from the 25934 nucleotide sequences. These primers can then be used for PCR screening of somatic cell hybrids containing individual human chromosomes. Only those hybrids containing the human gene corresponding to the 25934 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 25934 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the 25934 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 25934 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 25934 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 25934 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 25934 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 25934 nucleotide sequences described herein can further be used to provide polynucleotide reagents, e.g., labeled or labelable probes which can be used in, for example, an in situ hybridization technique, to identify a specific tissue, e.g., a tissue containing 25934. This can be very useful in cases where a forensic pathologist is presented with a tissue of unknown origin. Panels of such 25934 probes can be used to identify tissue by species and/or by organ type.

In a similar fashion, these reagents, e.g., 25934 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 25934.

Such disorders include, e.g., a disorder associated with the misexpression 25934; a disorder associated with unsaturation of fatty acids, e.g., cardiovascular, diabetes, obesity, hypertension, cancer, and neurological diseases.

The method includes one or more of the following:

detecting, in a tissue of the subject, the presence or absence of a mutation which affects the expression of the 25934 gene, or detecting the presence or absence of a mutation in a region which controls the expression of the gene, e.g., a mutation in the 5' control region;

detecting, in a tissue of the subject, the presence or absence of a mutation which alters the structure of the 25934 gene;

detecting, in a tissue of the subject, the misexpression of the 25934 gene, at the mRNA level, e.g., detecting a non-wild type level of a mRNA;

detecting, in a tissue of the subject, the misexpression of the gene, at the protein level, e.g., detecting a non-wild type level of a 25934 polypeptide.

In preferred embodiments the method includes: ascertaining the existence of at least one of: a deletion of one or more nucleotides from the 25934 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 25934 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 2593 gene; the presence of a non-wild type splicing pattern of a messenger RNA transcript of the gene; or a non-wild type level of 25934.

Methods of the invention can be used prenatally or to determine if a subject's offspring will be at risk for a disorder.

In preferred embodiments the method includes determining the structure of a 25934 gene, an abnormal structure being indicative of risk for the disorder.

In preferred embodiments the method includes contacting a sample form the subject with an antibody to the 25934 protein or a nucleic acid, which hybridizes specifically with the gene. There and other embodiments are discussed below.

Diagnostic and Prognostic Assays

The presence, level, or absence of 25934 protein or nucleic acid in a biological sample can be evaluated by obtaining a biological sample from a test subject and contacting the biological sample with a compound or an agent capable of detecting 25934 protein or nucleic acid (e.g., mRNA, genomic DNA) that encodes 25934 protein such that the presence of 25934 protein or nucleic acid is detected in the biological sample. The term "biological sample" includes tissues, cells and biological fluids isolated from a subject, as well as tissues, cells and fluids present within a subject. A preferred biological sample is serum. The level of expression of the 25934 gene can be measured in a number of ways, including, but not limited to: measuring the mRNA encoded by the 25934 genes; measuring the amount of protein encoded by the 25934 genes; or measuring the activity of the protein encoded by the 25934 genes.

The level of mRNA corresponding to the 25934 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 25934 nucleic acid, such as the nucleic acid of SEQ ID NO:1, or the DNA insert of the plasmid deposited with ATCC as Accession Number 2167, or a portion thereof, such as an oligonucleotide of at least 7, 15, 30, 50, 100, 250 or 500 nucleotides in length and sufficient to specifically hybridize under stringent conditions to 25934 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 25934 genes.

The level of mRNA in a sample that is encoded by one of 25934 can be evaluated with nucleic acid amplification, e.g., by rtPCR (Mullis, 1987, U.S. Pat. No. 4,683,202), ligase chain reaction (Barany, 1991, Proc. Natl. Acad. Sci. USA 88:189–193), self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 25934 gene being analyzed.

In another embodiment, the methods further contacting a control sample with a compound or agent capable of detecting 25934 mRNA, or genomic DNA, and comparing the presence of 25934 mRNA or genomic DNA in the control sample with the presence of 25934 mRNA or genomic DNA in the test sample.

A variety of methods can be used to determine the level of protein encoded by 25934. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 25934 protein in a biological sample in vitro as well as in vivo. In vitro techniques for detection of 25934 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 25934 protein include introducing into a subject a labeled anti-25934 antibody. For example, the antibody can be labeled with a radioactive marker whose presence and location in a subject can be detected by standard imaging techniques.

In another embodiment, the methods further include contacting the control sample with a compound or agent capable of detecting 25934 protein, and comparing the presence of 25934 protein in the control sample with the presence of 25934 protein in the test sample.

The invention also includes kits for detecting the presence of 25934 in a biological sample. For example, the kit can include a compound or agent capable of detecting 25934 protein or mRNA in a biological sample; and a standard. The compound or agent can be packaged in a suitable container. The kit can further comprise instructions for using the kit to detect 25934 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 25934 expression or activity. As used herein, the term "unwanted" includes an unwanted phenomenon involved in a biological response such as pain or deregulated cell proliferation.

In one embodiment, a disease or disorder associated with aberrant or unwanted 25934 expression or activity is identified. A test sample is obtained from a subject and 25934 protein or nucleic acid (e.g., mRNA or genomic DNA) is evaluated, wherein the level, e.g., the presence or absence, of 25934 protein or nucleic acid is diagnostic for a subject having or at risk of developing a disease or disorder associated with aberrant or unwanted 25934 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 25934 expression or activity. For example, such methods can be used to determine whether a subject can be effectively treated with an agent for a cell disorder associated with abnormal or abherrant unsaturation of fatty acids.

The methods of the invention can also be used to detect genetic alterations in a 25934 gene, thereby determining if a subject with the altered gene is at risk for a disorder characterized by misregulation in 25934 protein activity or nucleic acid expression, such as as in the following disorders: cardiovascular, diabetes, obesity, hypertension, cancer, developmental disorders, immune disorders and neurological diseases.

In preferred embodiments, the methods include detecting, in a sample from the subject, the presence or absence of a genetic alteration characterized by at least one of an alteration affecting the integrity of a gene encoding a 25934-protein, or the mis-expression of the 25934 gene. For example, such genetic alterations can be detected by ascertaining the existence of at least one of 1) a deletion of one or more nucleotides from a 25934 gene; 2) an addition of one or more nucleotides to a 25934 gene; 3) a substitution of one or more nucleotides of a 25934 gene, 4) a chromosomal rearrangement of a 25934 gene; 5) an alteration in the level of a messenger RNA transcript of a 25934 gene, 6) aberrant modification of a 25934 gene, such as of the methylation pattern of the genomic DNA, 7) the presence of a non-wild type splicing pattern of a messenger RNA transcript of a 25934 gene, 8) a non-wild type level of a 25934-protein, 9) allelic loss of a 25934 gene, and 10) inappropriate post-translational modification of a 25934-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 25934-gene. This method can include the steps of collecting a sample of cells from a subject, isolating nucleic acid (e.g., genomic, mRNA or both) from the sample, contacting the nucleic acid sample with one or more primers which specifically hybridize to a 25934 gene under conditions such that hybridization and amplification of the 25934-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or other nucleic acid amplification methods, followed by the detection of the amplified molecules using techniques known to those of skill in the art.

In another embodiment, mutations in a 25934 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 25934 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 25934 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 25934 gene and detect mutations by comparing the sequence of the sample 25934 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 25934 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 25934 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 25934 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 25934 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1 985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 25934 gene.

Use of 25934 Molecules as Surrogate Markers

The 25934 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 25934 molecules of the invention may be detected, and may be correlated with one or more biological states in vivo. For example, the 25934 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 25934 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 25934 marker) transcription or expression, the amplified marker may be in a quantity which is more readily detectable than the drug itself. Also, the marker may be more easily detected due to the nature of the marker itself; for example, using the methods described herein, anti-25934 antibodies may be employed in an immune-based detection system for a 25934 protein marker, or 25934-specific radiolabeled probes may be used to detect a 25934 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3:S16–S20.

The 25934 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 25934 protein or RNA) for specific tumor markers in a subject, a drug or course of treatment may be selected that is optimized for the treatment of the specific tumor likely to be present in the subject. Similarly, the presence or absence of a specific sequence mutation in 25934 DNA may correlate 25934 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-25934 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 25934 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 25934 molecules of the present invention or 25934 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 25934 expression or activity, by administering to the subject a 25934 or an agent which modulates 25934 expression or at least one 25934 activity. Subjects at risk for a disease which is caused or contributed to by aberrant or unwanted 25934 expression or activity can be identified by, for example, any or a combination of diagnostic or prognostic assays as described herein. Administration of a prophylactic agent can occur prior to the manifestation of symptoms characteristic of the 25934 aberrance, such that a disease or disorder is prevented or, alternatively, delayed in its progression. Depending on the type of 25934 aberrance, for example, a 25934, 25934 agonist or 25934 antagonist agent can be used for treating the subject. The appropriate agent can be determined based on screening assays described herein.

It is possible that some 25934 disorders can be caused, at least in part, by an abnormal level of gene product, or by the presence of a gene product exhibiting abnormal activity. As such, the reduction in the level and/or activity of such gene products would bring about the amelioration of disorder symptoms.

In addition to the cardiovascular indications described above, the 25934 molecules of the invention can be used to treat, prevent and/or diagnose disorders involving the cells in which the 25934 mRNA is expressed (FIGS. 4–6). Accordingly, the molecules of the invention can be used to treat, present and/or diagnose neurological, reproductive (ovarian), renal, metabolic and hepatic disorders.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the liver include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 25934 molecules may play an important role in the etiology of certain viral diseases, inducing but not limited to Hepatitis B, Heptitis C and Herpes Simplex Virus (HSV). Modulators of 25934 activity could be used to control viral diseases. The modulators can be used in the treatment and/or diagnosis of viral infected tissue or virus-associated tissue fibrosis, especially liver and liver fibrosis. Also, 25934 modulators can be used in the treatment and/or diagnosis of virus-associated carcinoma, especially hepatocellular cancer.

Additionally, 25934 may play an important role in the regulation of metabolism. Diseases of metabolic imbalance include, but are not limited to, obesity, anorexia nervosa, cachexia, lipid disorders diabetes.

As discussed, successful treatment of 25934 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 25934 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 25934 expression is through the use of aptamer molecules specific for 25934 protein. Aptamers are nucleic acid molecules having a tertiary structure which permits them to specifically bind to protein ligands (see, e.g., Osborne, et al. Curr. Opin. Chem Biol. 1997, 1(1): 5–9; and Patel, D. J. Curr Opin Chem Biol 1997 June;1(1):32–46). Since nucleic acid molecules may in many cases be more conveniently introduced into target cells than therapeutic protein molecules may be, aptamers offer a method by which 25934 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 25934 disorders. For a description of antibodies, see the Antibody section above.

In circumstances wherein injection of an animal or a human subject with a 25934 protein or epitope for stimulating antibody production is harmful to the subject, it is possible to generate an immune response against 25934 through the use of anti-idiotypic antibodies (see, for example, Herlyn, D. *Ann Med* 1999;31(1):66–78; and Bhattacharya-Chatterjee, M., and Foon, K. A. *Cancer Treat Res* 1998;94:51–68). If an anti-idiotypic antibody is introduced into a mammal or human subject, it should stimulate the production of anti-anti-idiotypic antibodies, which should be specific to the 25934 protein. Vaccines directed to a disease characterized by 25934 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, Proc. Natl. Acad. Sci. USA 90:7889–7893).

The identified compounds that inhibit target gene expression, synthesis and/or activity can be administered to a patient at therapeutically effective doses to prevent, treat or ameliorate 25934 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 25934 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 25934 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 25934 expression or activity for therapeutic purposes. Accordingly, in an exemplary embodiment, the modulatory method of the invention involves contacting a cell with a 25934 or agent that modulates one or more of the activities of 25934 protein activity associated with the cell. An agent that modulates 25934 protein activity can be an agent as described herein, such as a nucleic acid or a protein, a naturally-occurring target molecule of a 25934 protein (e.g., a 25934 substrate or receptor), a 25934 antibody, a 25934 agonist or antagonist, a peptidomimetic of a 25934 agonist or antagonist, or other small molecule.

In one embodiment, the agent stimulates one or 25934 activities. Examples of such stimulatory agents include active 25934 protein and a nucleic acid molecule encoding 25934. In another embodiment, the agent inhibits one or more 25934 activities. Examples of such inhibitory agents include antisense 25934 nucleic acid molecules, anti25934 antibodies, and 25934 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 25934 protein or nucleic acid molecule. In one embodiment, the method involves administering an agent (e.g., an agent identified by a screening assay described herein), or combination of agents that modulates (e.g., upregulates or downregulates) 25934 expression or activity. In another embodiment, the method involves administering a 25934 protein or nucleic acid molecule as therapy to compensate for reduced, aberrant, or unwanted 25934 expression or activity.

Stimulation of 25934 activity is desirable in situations in which 25934 is abnormally downregulated and/or in which increased 25934 activity is likely to have a beneficial effect. For example, stimulation of 25934 activity is desirable in situations in which a 25934 is downregulated and/or in which increased 25934 activity is likely to have a beneficial effect. Likewise, inhibition of 25934 activity is desirable in situations in which 25934 is abnormally upregulated and/or in which decreased 25934 activity is likely to have a beneficial effect.

Pharmacogenomics

The 25934 molecules of the present invention, as well as agents, or modulators which have a stimulatory or inhibitory effect on 25934 activity (e.g., 25934 gene expression) as identified by a screening assay described herein can be administered to individuals to treat (prophylactically or therapeutically) 25934 associated disorders (e.g., diabetes, obesity, hypertension, cancer, developmental disorders, immune disorders and neurological and heart diseases) associated with aberrant or unwanted 25934 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 25934 molecule or 25934 modulator as well as tailoring the dosage and/or therapeutic regimen of treatment with a 25934 molecule or 25934 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11):983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 25934 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 25934 molecule or 25934 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 25934 molecule or 25934 modulator, such as a modulator identified by one of the exemplary screening assays described herein.

The present invention further provides methods for identifying new agents, or combinations, that are based on identifying agents that modulate the activity of one or more of the gene products encoded by one or more of the 25934 genes of the present invention, wherein these products may be associated with resistance of the cells to a therapeutic agent. Specifically, the activity of the proteins encoded by the 25934 genes of the present invention can be used as a basis for identifying agents for overcoming agent resistance. By blocking the activity of one or more of the resistance proteins, target cells, e.g., adipocyte cells, will become sensitive to treatment with an agent that the unmodified target cells were resistant to.

Monitoring the influence of agents (e.g., drugs) on the expression or activity of a 25934 protein can be applied in clinical trials. For example, the effectiveness of an agent determined by a screening assay as described herein to increase 25934 gene expression, protein levels, or upregulate 25934 activity, can be monitored in clinical trials of subjects exhibiting decreased 25934 gene expression, protein levels, or downregulated 25934 activity. Alternatively, the effectiveness of an agent determined by a screening assay to decrease 25934 gene expression, protein levels, or downregulate 25934 activity, can be monitored in clinical trials of subjects exhibiting increased 25934 gene expression, protein levels, or upregulated 25934 activity. In such clinical trials, the expression or activity of a 25934 gene, and preferably, other genes that have been implicated in, for example, a 25934-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 25934, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 25934 nucleic acid, polypeptide, or antibody.

The capture probes can be a set of nucleic acids from a selected sample, e.g., a sample of nucleic acids derived from a control or non-stimulated tissue or cell.

The method can include contacting the 25934 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 25934. Such methods can be used to diagnose a subject, e.g., to evaluate risk for a disease or disorder, to evaluate suitability of a selected treatment for a subject, to evaluate whether a subject has a disease or disorder. 25934 is associated with regulating membrane fluidity, thus it is useful for evaluating a number of diseases such as diabetes, obesity, hypertension, cancer, developmental disorders, immune disorders and neurological and heart diseases.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 25934 or from a cell or subject in which a 25934 mediated response has been elicited, e.g., by contact of the cell with 25934 nucleic acid or protein, or administration to the cell or subject 25934 nucleic acid or protein; contacting the array with one or more inquiry probe, wherein an inquiry probe can be a nucleic acid, polypeptide, or antibody (which is preferably other than 25934 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 25934 (or does not express as highly as in the case of the 25934 positive plurality of capture probes) or from a cell or subject which in which a 25934 mediated response has not been elicited (or has been elicited to a lesser extent than in the first sample); contacting the array with one or more inquiry probes (which is preferably other than a 25934 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 25934, e.g., analyzing structure, function, or relatedness to other nucleic acid or amino acid sequences. The method includes: providing a 25934 nucleic acid or amino acid sequence; comparing the 25934 sequence with one or more preferably a plurality of sequences from a collection of sequences, e.g., a nucleic acid or protein sequence database; to thereby analyze 25934.

Preferred databases include Genbank. The method can include evaluating the sequence identity between a 25934 sequence and a database sequence. The method can be performed by accessing the database at a second site, e.g., over the internet.

In another aspect, the invention features, a set of oligonucleotides, useful, e.g., for identifying SNP's, or identifying specific alleles of 25934. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with diferential labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1

Identification and Characterization of Human 25934 cDNA

The human 25934 sequence (FIGS. 1A–B; SEQ ID NO:1), which is approximately 1512 nucleotides long including untranslated regions, contains a predicted methionine-initiated coding sequence of about 990 nucleotides (nucleotides 403 to 1392 of SEQ ID NO:1; SEQ ID NO:3). The coding sequence encodes a 330 amino acid protein (SEQ ID NO:2).

Example 2

Tissue Distribution of 25934 mRNA

Endogenous human 25934 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 25934 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction.

25934 mRNA levels were analyzed in a variety of samples of isolated from the human fetal heart, spinal cord, brain (cortex, hypothalamus, glial cells), ovary, kidney, liver, endothelial cells and smooth muscle cells (SMC). The highest relative 25934 mRNA expression, i.e., greater than 200 relative units, was observed in spinal cord, brain and ovary (FIG. 4). High level mRNA expression, i.e., greater than 100 relative units was observed in the kidney, endothelial cells and human umbilical vein endothelial cells (HUVEC) (FIG. 4). Expression in liver (a target organ for 25934) was positive but lower relative to other tissues.

The relative 25934 mRNA expression as determined by TaqMan assays on mRNA derived a panel of human liver tissues is shown in FIG. 5. FIG. 6 shows a comparison of the expression of 25934 mRNA and stearoyl CoA desaturase (SCD) mRNA in a panel of human liver. Expression of 25934 mRNA in human liver is equivalent to the relative expression of the known SCD gene.

FIG. 7 shows the inhibition of 25934 mRNA expression in the marmoset animal model. Niacin treatment in the marmoset model results in significant repression of 25934 in the liver.

Northern blot hybridizations with various RNA samples can be performed under standard conditions and washed under stringent conditions, i.e., 0.2×SSC at 65° C. A DNA probe corresponding to all or a portion of the 25934 cDNA (SEQ ID NO:1) is used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) is probed in ExpressHyb hybridization solution (Clontech) and washed at high stringency according to manufacturer's recommendations.

Example 3

Recombinant Expression of 25934 in Bacterial Cells

In this example, 25934 is expressed as a recombinant glutathione-S-transferase (GST) fusion polypeptide in *E. coli* and the fusion polypeptide is isolated and characterized. Specifically, 25934 is fused to GST and this fusion polypeptide is expressed in *E. coli*, e.g., strain PEB199. Expression of the GST-25934 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 25934 Protein in COS Cells

To express the 25934 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 25934 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 25934 DNA sequence is amplified by PCR using two primers. The 5' primer contains the restriction site of interest followed by approximately twenty nucleotides of the 25934 coding sequence starting from the initiation codon; the 3' end sequence contains complementary sequences to the other restriction site of interest, a translation stop codon, the HA tag or FLAG tag and the last 20 nucleotides of the 25934 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 25934 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 25934-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed, Cold Spring Harbor Laboratory,* Cold Spring Harbor Laboratory Press, Cold Spring Harbor, N.Y., 1989. The expression of the 25934 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 25934 coding sequence is cloned directly into the polylinker of the pcDNA/Amp vector using the appropriate restriction sites. The resulting plasmid is transfected into COS cells in the manner described above, and the expression of the 25934 polypeptide is detected by radiolabelling and immunoprecipitation using a 25934 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising a nucleotide sequence that encodes a polypeptide comprising the sequence of SEQ ID NO:2.

2. The nucleic acid of claim 1, wherein the polypeptide consists of the amino acid sequence of SEQ ID NO:2.

3. An isolated nucleic acid comprising the nucleotide sequence of SEQ ID NO:3 or a complete complement thereof.

4. The nucleic acid of claim 3, wherein the nucleic acid consists of the nucleotide sequence of SEQ ID NO:3.

5. The nucleic acid of claim 3, wherein the nucleic acid comprises the nucleotide sequence of SEQ ID NO:1 or a complete complement thereof.

6. An isolated nucleic acid comprising a nucleotide sequence that encodes a polypeptide comprising an amino acid sequence that is at least 80% identical to the sequence of SEQ ID NO:2 or the sequence encoded by the cDNA insert of the plasmid deposited with the ATCC as Accession Number 2167, wherein the percent identity is determined using the ALIGN program in the GCG software package, using a PAM120 weight residue table, a gap length penalty of 12, and a gap penalty of 4, and wherein the polypeptide has fatty acid desaturase activity.

7. The nucleic acid of claim 6, wherein the amino acid sequence is at least 90% identical to the sequence of SEQ ID NO:2 or the sequence encoded by the cDNA insert of the plasmid deposited with the ATCC as Accession Number 2167.

8. The nucleic acid of claim 7, wherein the amino acid sequence is at least 95% identical to the sequence of SEQ ID NO:2 or the sequence encoded by the cDNA insert of the plasmid deposited with the ATCC as Accession Number 2167.

9. The nucleic acid of claim 8, wherein the polypeptide comprises amino acid residues 51–295 of SEQ ID NO:2.

10. The nucleic acid of claim 6, further comprising a sequence encoding a heterologous polypeptide.

11. A vector comprising the nucleic acid of claim 6.

12. The vector of claim 11, wherein the vector comprises nucleic acid sequences which regulate expression of a polypeptide encoded by the nucleic acid.

13. A host cell comprising the vector of claim 12.

14. The host cell of claim 13, which is a mammalian host cell.

15. A method for producing a polypeptide, the method comprising culturing the host cell of claim 14 under conditions in which the nucleic acid is expressed to produce the polypeptide.

16. An isolated nucleic acid comprising a nucleotide sequence that is at least 80% identical to the nucleotide sequence of SEQ ID NO:3, wherein the percent identity is determined using the NBLAST program with a score of 100 and a word length of 12, and wherein the nucleotide sequence encodes a polypeptide having fatty acid desaturase activity.

17. The nucleic acid of claim 16, wherein the nucleotide sequence is at least 90% identical to the nucleotide sequence of SEQ ID NO:3.

18. The nucleic acid of claim 17, wherein the nucleotide sequence is at least 95% identical to the nucleotide sequence of SEQ ID NO:3.

19. The nucleic acid of claim 16, wherein the polypeptide comprises amino acid residues 51–295 of SEQ ID NO:2.

20. An isolated nucleic acid of at least 750 nucleotides in length comprising a nucleotide sequence that hybridizes to the sequence of SEQ ID NO:3 or the complete complement thereof under conditions of hybridization at 45° C. in 6.0×sodium chloride/sodium citrate (SSC) followed by one or more washes in 0.2×SSC, 0.1% SDS at 65° C., wherein the nucleotide sequence encodes a polypeptide having fatty acid desaturase activity.

21. The nucleic acid of claim 20 wherein the nucleic acid comprises at least 800 nucleotides.

22. The nucleic acid of claim 21, wherein the nucleic acid comprises at least 1000 nucleotides.

23. The nucleic acid of claim 22, wherein the nucleic acid comprises at least 1200 nucleotides.

24. The nucleic acid of claim 23, wherein the nucleic acid comprises at least 1400 nucleotides.

* * * * *